United States Patent
Heki

(10) Patent No.: US 6,200,299 B1
(45) Date of Patent: *Mar. 13, 2001

(54) DISPOSABLE DIAPER HAVING STRESS RELAXING STRUCTURES AND FASTENERS POSITIONED FOR IMPROVED FIT

(75) Inventor: Yukio Heki, Hyogo (JP)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/860,912

(22) PCT Filed: Jan. 2, 1996

(86) PCT No.: PCT/US96/00529

§ 371 Date: May 6, 1998

§ 102(e) Date: May 6, 1998

(87) PCT Pub. No.: WO96/21412

PCT Pub. Date: Jul. 18, 1996

(30) Foreign Application Priority Data

Jan. 11, 1995 (JP) .................................................. 7-018670

(51) Int. Cl.$^7$ .................................................. A61F 13/20

(52) U.S. Cl. .......................................................... 604/386

(58) Field of Search .................................. 604/385.1–386, 604/381, 350, 391, 392–394, 396

(56) References Cited

U.S. PATENT DOCUMENTS

| 5,496,298 | * | 3/1996 | Kuepper et al. | 604/385.2 |
| 5,554,145 | * | 9/1996 | Roe et al. | 604/387 |
| 5,580,411 | * | 12/1996 | Nease et al. | 604/385.1 |
| 5,593,401 | * | 1/1997 | Sosalla et al. | 604/387 |
| 5,906,008 | * | 5/1999 | Heki et al. | 604/385.01 |

FOREIGN PATENT DOCUMENTS

| 0 323 040 A1 | 7/1989 | (EP) . |
| WO 92/22274 | 12/1992 | (WO) . |
| WO 94/07450 | 4/1994 | (WO) . |
| WO 94/28841 | 12/1994 | (WO) . |
| 9428840 | * 12/1994 | (WO) ................................. 604/385.1 |

* cited by examiner

Primary Examiner—John G. Weiss
Assistant Examiner—David J. Cho
(74) Attorney, Agent, or Firm—Michael S. Kolodesh; David M. Weirich; Ken K. Patel

(57) ABSTRACT

A disposable diaper comprises an absorbent part, a pair of ear parts projecting in opposite directions from the opposite side edges of one longitudinal end portion of the absorbent part, respectively, and two fastening means attached to the side edges of the ear parts, respectively. Each side edge has a first side edge section and a second side edge section, each ear part has a stress relaxing structure, in which a tensile stress smaller than that which is induced in the peripheral portion of the ear part is induced, in a portion thereof other than the peripheral portion, and each fastening means is attached to the ear part in a pulling section of the side edge, overlapping at least part of a first side edge section and part of a second side edge section so that component tensile forces of a tensile force applied to the fastening means are distributed at a desired distribution ratio to the waist lapping portion and the leg lapping portion of the absorbent part.

10 Claims, 29 Drawing Sheets

DISPOSABLE DIAPER HAVING STRESS RELAXING STRUCTURES AND FASTENERS POSITIONED FOR IMPROVED FIT

BACKGROUND OF THE INVENTION

1. Field of the Invention

The present invention relates to a disposable diaper having an absorbent part, a pair of ear parts projecting in opposite directions from the side edges of one longitudinal end portion of the absorbent part, and two fastening means provided on the side edges of the ear parts, respectively, and capable of effectively distributing tensile forces applied to the absorbent part by the fastening means around the waist and around the legs to prevent the leakage of liquid excrement through spaces between the edges of the disposable diaper and the wearer's waist and legs and of giving comfort to the wearer.

1. Description of the Related Art

A generally known disposable diaper comprises an absorbent part for covering the wearer's crotch, formed by sandwiching an absorbent core between a top sheet and a back sheet, a pair of ear parts projecting in opposite directions from the side edges of one longitudinal end portion of the absorbent part so as to lap around the wearer's waist, and two fastening means provided on the side edges of the ear parts, respectively. When using this disposable diaper, the disposable diaper is put on the wearer in an ordinary manner, and then the fastening means are attached to portions of the absorbent part lapping around the waist, on the opposite sides of the fastening means, respectively, to hold the disposable diaper on the wearer. When thus put on the wearer, the disposable diaper must fit to the wearer's waist and legs so that any spaces through which liquid excrement will leak may not be formed between the disposable diaper and the wearer's waist and legs. When putting the disposable diaper provided with the fastening means provided on the side edges of the ear parts, respectively, on the wearer, it is difficult to concentrate the tensile forces applied to the absorbent part by the fastening means effectively on portions of the absorbent part lapped around the wearer's waist and legs, that is, spaces are formed around the wearer's legs and liquid excrement leaks outside through the spaces around the legs if the disposable diaper is fitted to the wearer's waist, or spaces are formed around the wearer's waist and the disposable diaper cannot lap fitly around the wearer's waist and liquid excrement leaks outside through the spaces around the waist if the disposable diaper is fitted to the wearer's legs.

Various improvements have been proposed to solve such problems and to improve the fit of a disposable diaper to the wearer's waist and legs. Techniques for improving the fit of a disposable diaper to both the waist and the legs are disclosed in U.S. Pat. No. 4,680,030 to Aled, et al., U.S. Pat. No. 4,826,499 to Ahr and U.S. Pat. No. 4,937,887 to Schreiner, which use two pairs of fastening means attached to a pair of ear parts projecting in opposite directions from a portion of the disposable diaper to be lapped around the waist, respectively. These prior art disposable diapers, however, require troublesome work for handling the two pairs of fastening means and there is room for improvement in those prior art disposable diapers. Techniques eliminating such a disadvantage are disclosed in U.S. Pat. No. 4,911,702 to O'Leary and U.S. Pat. No. 4,857,067 to Wood, which use two fastening means attached to two ear parts, respectively, and capable of effectively concentrating the tensile forces applied thereto on portions of the absorbent part lapped around the waist and the legs. However, these techniques mention nothing about the positions of the two fastening means to distribute the tensile forces applied to the two fastening means effectively and directly around the waist and the legs and about the positions of the two fastening means to distribute the tensile forces applied to the two fastening means around the waist and the legs at an intentionally determined distribution ratio.

SUMMARY OF THE INVENTION

Accordingly, it is a first object of the present invention to provide a disposable diaper having an absorbent part provided with fastening means positioned so that tensile forces applied thereto are distributed at a desired distribution ratio to a waist lapping section of the absorbent part lapped around the waist and to leg lapping sections of the same lapped around the legs.

A second object of the present invention is to provide a disposable diaper having an absorbent part having leg lapping sections to be lapped around the legs, provided with elastic leg fastening members, respectively, and fastening means disposed so that the tensile forces applied thereto may be effectively and directly concentrated on a waist lapping section of the absorbent part lapped around the waist and on the elastic leg fastening members.

A third object of the present invention is to provide a disposable diaper having an absorbent part having a waist lapping section provided with elastic waist fastening members, and leg lapping sections provided with elastic leg fastening members and fastening means positioned so that the tensile forces applied thereto may be effectively and directly concentrated on the elastic leg fastening members and the elastic waist fastening members.

In a first aspect of the present invention, a disposable diaper comprises: an absorbent part formed by sandwiching an absorbent core between a top sheet and a back sheet so that the absorbent core may correspond to the wearer's crotch when the disposable diaper is put on the wearer; a pair of ear parts projecting in opposite directions from the opposite side edges of one longitudinal end portion of the absorbent part, respectively; and two fastening means attached to the side edges of the ear parts, respectively. In this disposable diaper, each ear part has a stress relaxing structure, in which a tensile stress smaller than that which is induced in the peripheral portion of the ear part is induced, in a portion thereof other than the peripheral portion, and each fastening means is attached to the ear part in a pulling section of the side edge of the ear part, overlapping at least part of a first side edge section extending on the side of one longitudinal end edge of the absorbent part corresponding to the ear part from a first boundary line extending from a point on the one longitudinal end edge so as to be tangent to the stress relaxing structure, and part of a second side edge section extending on the side of the transverse center axis of the absorbent part perpendicular to the longitudinal center axis of the absorbent part from a second boundary line extending from a point on the side edge of the absorbent part so as to be tangent to the stress relaxing structure.

The degree of overlap of the pulling section with the first side edge section and the degree of overlap of the same with the second side edge section can be optionally determined. Those degrees of overlap may be different from or equal to each other, the former may be greater than the latter or the latter may be greater than the former. Each fastening means may be attached to the ear part at an angle to the side edge of the ear part.

In a second aspect of the present invention, a disposable diaper comprises: an absorbent part formed by sandwiching an absorbent core between a top sheet and a back sheet so that the absorbent core may correspond to the wearer's crotch when the disposable diaper is put on the wearer, and having a first waist lapping section and a second waist lapping section contiguous with the first and the second longitudinal end edge, respectively; a crotch lapping section extending between the first and the second waist lapping section and around the transverse center axis of the absorbent part; elastic leg fastening means extending along the opposite longitudinal side edges of the crotch lapping section of the absorbent part, respectively; a pair of ear parts projecting from the opposite side edges of the first waist lapping section of the absorbent part; and two fastening means attached to the side edges of the ear parts, respectively. In this disposable diaper, each ear part has a stress relaxing structure, in which a tensile stress smaller than that which is induced in the peripheral portion of the ear part is induced, in a portion thereof other than the peripheral portion; a portion of the first waist lapping section, extending on the side of the first longitudinal end edge from a first boundary line extending from a point on the first longitudinal end edge so as to be tangent to the stress relaxing structure is a waist lapping component force distributing region to which a component of a tensile force applied to the fastening means acts directly; a section of the side edge of the ear part corresponding to the waist lapping component force distributing region is a first side edge section; a portion of the first waist lapping section extending on the side of the crotch portion from a second boundary line extending from one end of the elastic leg fastening means on the side of the first waist lapping section so as to be tangent to the stress relaxing structure is a leg lapping component force distributing region to which a component of a tensile force applied to the fastening means acts directly; a section of the side edge of the ear part corresponding to the leg lapping component force distributing region is a second side edge section; and each fastening means attached to the ear part in a pulling section of the side edge of the ear part, overlapping at least part of the first side edge section and part of the second side edge section.

In a third aspect of the present invention, a disposable diaper comprises; an absorbent part formed by sandwiching an absorbent core between a top sheet and a back sheet so that the absorbent core may correspond to the wearer's crotch when the disposable diaper is put on the wearer, and having a first waist lapping section and a second waist lapping section contiguous with the first and the second longitudinal end edge, respectively; a crotch lapping section extending between the first and the second waist lapping sections around the transverse center axis of the absorbent part; elastic waist fastening means extending along the first longitudinal end edge of the first waist lapping section; a pair of ear parts projecting from the opposite side edges of the first waist lapping section of the absorbent part; and two fastening means attached to the side edges of the ear parts, respectively. In this disposable diaper, each ear part has a stress relaxing structure, in which a tensile stress smaller than that which is induced in the peripheral portion of the ear part is induced, in a portion thereof other than the peripheral portion; a portion of the first waist lapping section extending on the side of the first longitudinal end edge from a first boundary line extending from one end of the elastic waist fastening means on the side of the ear part so as to be tangent to the stress relaxing structure is a waist lapping component force distributing region to which a component of the tensile force applied to the fastening means acts directly; a section of the side edge of the ear part corresponding to the waist lapping component force distributing region is a first side edge section; a portion of the first waist lapping section, extending on the side of the crotch lapping section from a second boundary line extending from position where the lower end of the ear part joins to the longitudinal side edge of the crotch lapping section so as to be tangent to the stress relaxing structure is a leg lapping component force distributing region to which a component of the tensile force applied to the fastening means acts directly; a section of the side edge of the ear part corresponding to the leg lapping component force distributing portion is a second side edge section; and the fastening means attached to the ear part in a pulling section of the side edge, overlapping at least part of the first side edge section and part of the second side edge section.

The stress relaxing structure of the ear part, formed in a portion other than the peripheral portion of the ear part, in which a tensile stress smaller than that which is induced in the peripheral portion, absorbs the tensile force applied thereto through the fastening means, and the peripheral portion of the ear part transmits the tensile force directly to the absorbent part, so that the tensile force applied to the fastening means can be effectively and directly applied to the waist lapping section and the leg lapping section of the absorbent part.

Attachment of the fastening means to the side edge of the ear part in the pulling section overlapping at least part of the first side edge section and the second side edge section defined in positional connection with the absorbent part and the stress relaxing structure of the ear part ensures the application of the tensile force applied to the fastening means to part of the first longitudinal end edge of the absorbent part on the side of the first waist lapping section or to part of the edge of the ear part on the side of the transverse center axis of the disposable diaper.

The tensile force that acts on part of the longitudinal end edge of the absorbent part on the side of the first waist lapping section or on part of the edge of the ear part on the side of the transverse center axis of the disposable diaper can be adjusted by adjusting the degree of overlap of the pulling section in which the fastening means is attached to the ear part with the first side edge section or the second side edge section. A major part of the tensile force applied to the fastening means is applied to the first waist lapping section when the degree of overlap of the pulling section with the first side edge section is greater than that with the second side edge section, and to a portion of the end edge of the ear part on the side of the transverse center axis of the disposable diaper when degree of overlap of the pulling section with the first side edge section is smaller than that with the second side edge section.

The distribution of the tensile force can be adjusted by selectively determining the angle of the fastening means to the side edge of the ear part. When the fastening means is inclined obliquely upward, a major part of the tensile force applied to the fastening means is distributed to the leg lapping section of the disposable diaper. When the fastening means is declined obliquely downward, a major part of the tensile force applied to the fastening means is distributed to the first waist lapping section.

Determination of the first side edge section in connection with the end of the elastic waist fastening means and that of the second side edge section in connection with the end of the elastic leg fastening means ensures the distribution of the tensile force applied to the fastening means to the elastic waist fastening means and the elastic leg fastening means.

The above and other objects, features and advantages of the present invention will become more apparent from the following description taken in connection with the accompanying drawings.

BRIEF DESCRIPTION OF THE DRAWINGS

FIG. 22 is a fragmentary development showing a fastening means attached to an ear part in a pulling section having a minor portion overlapping a second side edge section b and a major portion overlapping a first side edge section a;

FIG. 23 is a fragmentary development showing a fastening member attached to an ear part in a pulling section having a major portion overlapping a second side edge section b and a minor portion overlapping a first side edge section a;

DESCRIPTION OF THE PREFERRED EMBODIMENTS

Figure 1:
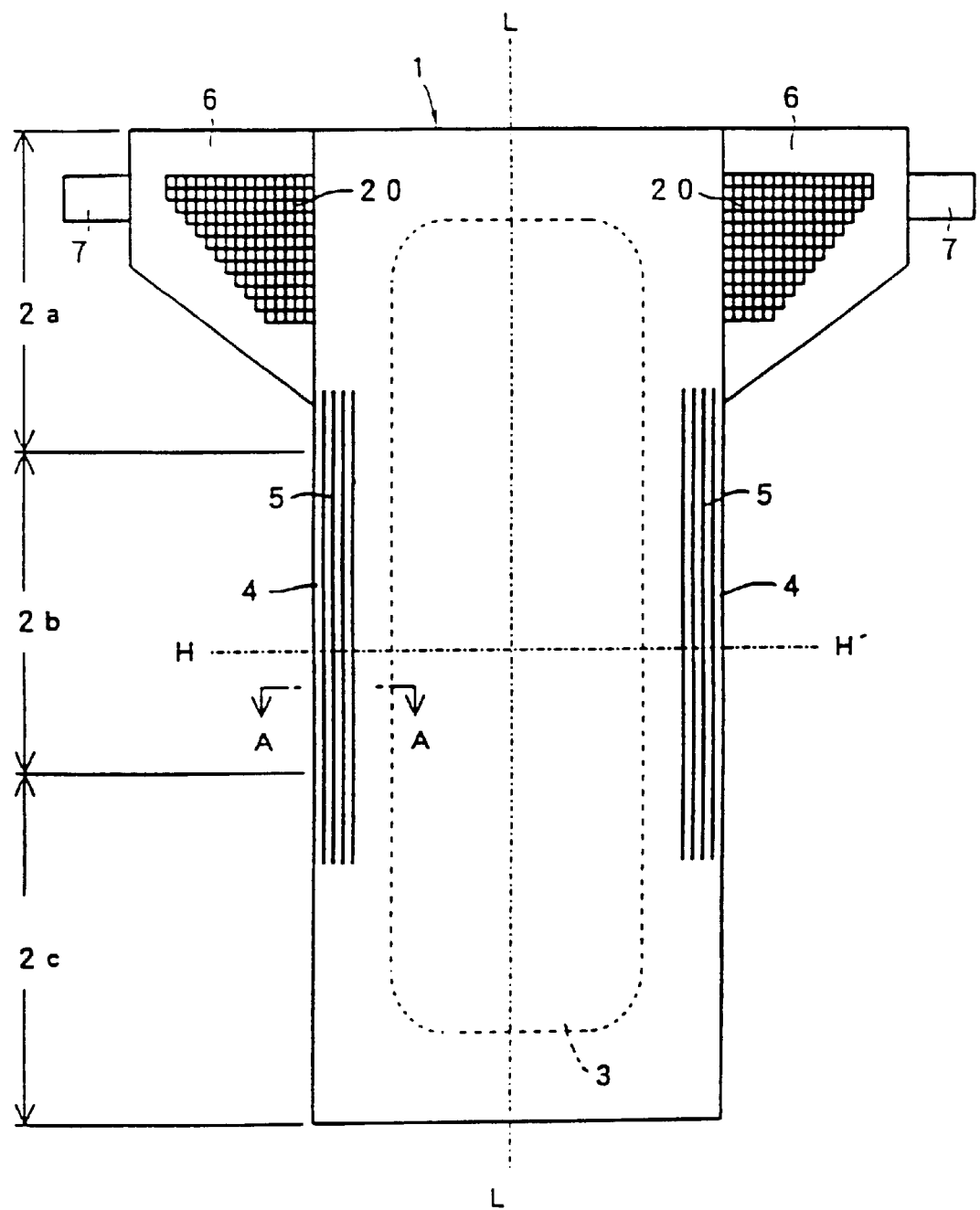
FIG. 1 is a development of a disposable diaper in accordance with the present invention.

In the following description, terms expressing positions, directions and the like indicate those as viewed in the drawings.

Referring to FIG. 1, a disposable diaper 1 in a first embodiment according to the present invention has a first waist lapping section 2a, a crotch lapping section 2b and a second waist lapping section 2c, and comprises an absorbent part formed substantially in a rectangular shape, an hour glass shape, a T-shape, an asymmetric shape or such, side flaps 4 formed in the opposite side portions of the absorbent part 3, respectively, elastic leg fastening members 5 longitudinally extended in the flaps 4 to provide the flaps 4 with elasticity, a pair of ear parts 6 projecting in opposite directions from the opposite side edges of the upper end portion of the first waist lapping section 2a of the absorbing part 3, respectively, and two fasteners 7 attached to the side edges 6a of the ear parts 6, respectively.

Figure 2:
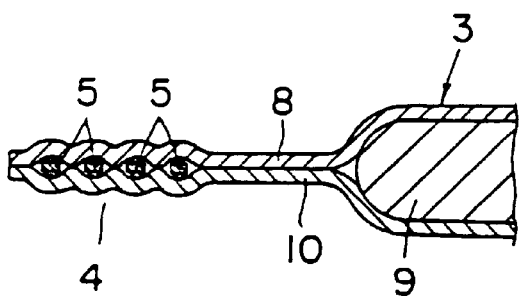
FIG. 2 is a fragmentary sectional view of an absorbent part of a disposable diaper in accordance with the present invention.

Referring to FIG. 2 showing a sectional view taken on line A—A in FIG. 1, the absorbent part 3 is formed by sandwiching an absorbent core 9 between a liquid-permeable top sheet 8 and a liquid-impermeable back sheet 10. The top sheet 8 and the back sheet 10 have a length and a width greater than those of the absorbent core 9. At least portions of the top sheet 8 and the back sheet 10, corresponding to the crotch lapping section 2b and extending outward beyond each longitudinal side edge of the absorbent core 9 form a side flap 4, and elastic leg fastening members 5 are extended longitudinally in the side flap 4 to provide the side flap with elasticity. The absorbent core 9 is unirritateive to the skin and capable of absorbing and holding liquid excrement including urine. Generally, the absorbent core 9 is formed of crushed wood pulp, generally cold cotton pulp. The absorbent core 9 may be formed in any suitable shape and construction as occasion demands. The total absorption of the absorbent core 9 must correspond to a design charge and a desired use. The size and the absorbing ability of the absorbent core 9 are dependent on the wearer's age.

The back sheet 10 prevents wetting an article, such as a bed sheet or underwear, that comes into contact with the disposable diaper 1 with excrement absorbed and held by the absorbent core 9. The back sheet 10 is a film of a thermoplastic polymer, such as a polyethylene film, a polypropylene film or the like, or a film of a composite material, such as film-coated nonwoven fabric. Preferably, the back sheet 10 is an embossed thermoplastic film simulating fabric. The top sheet 8 is a porous foam sheet, a meshed foam sheet, a perforated plastic film or a woven or nonwoven fabric of a natural textile material, such as wood fibers or cotton fibers, a synthetic textile material, such as polyester fibers or polypropylene fibers, or a blended textile material, such as a blend of a natural textile material (or natural textile materials) and a synthetic textile material (or synthetic textile materials). Preferably, the top sheet 8 is formed of a hydrophobic material to separate the liquid absorbed by the absorbent core 9 from the wearer's skin.

Figure 3:
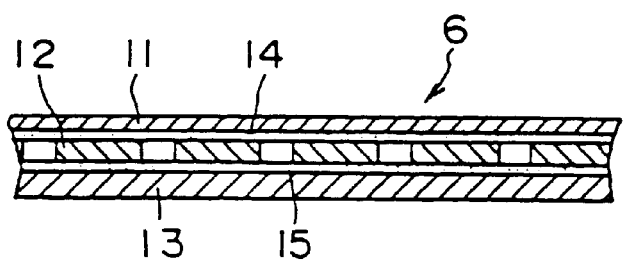
FIG. 3 is a fragmentary sectional view of an ear part.

The ear parts 6 having a substantially trapezoidal shape are joined to the opposite side edges of the first waist lapping section 2a of the rectangular absorbent part 3, respectively, by a known method, such as heat-sealing or adhesive bonding. The ear parts 6 may be formed integrally with the absorbent part 3 by projecting the respective upper side portions of the top sheet 8 and the back sheet 10 outward in lugs having the shape of the ear parts 6, and directly joining together the projecting lugs of the top sheet 8 and the back sheet 10. The absorbent part 3 and the ear parts 6 may be formed in an integral structure by cutting a laminated sheet formed by sandwiching a sheet between the top sheet 8 and the back sheet 10 in desired dimensions. Preferably, the ear parts 6 are formed by laminating a nonwoven fabric 11 of natural fibers, synthetic fibers or a blend of natural fibers and synthetic fibers, a thermoplastic film 13 of polyethylene or polypropylene, and a porous film 12 formed by a known process and sandwiched between the nonwoven fabric 11 and the thermoplastic film 13 by adhesive layers 14 and 15 as shown in FIG. 3. When each of the ear parts 6 is formed of an extension of the top sheet 8 and an extension of the back sheet 10, the nonwoven fabric 11 and the thermoplastic film 13 correspond to the extension of the top sheet 8 and the extension of the back sheet 10, respectively. The porous film 12 sandwiched between the nonwoven fabric 11 and the thermoplastic film 13 provides the ear parts 6 with firmness, which facilitates handling the ear parts 6 when putting the disposable diaper 1 on the wearer.

Figure 4:
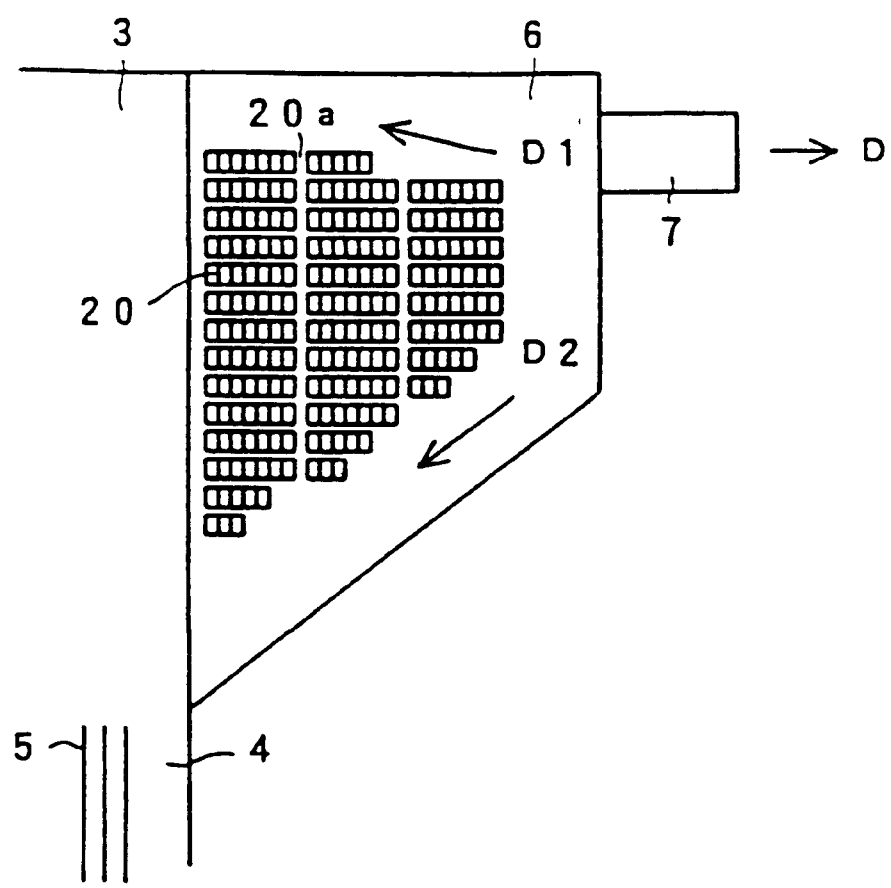
FIG. 4 is a plan view of a stress relaxing structure in a first example included in a disposable diaper in accordance with the present invention.
Figure 5:
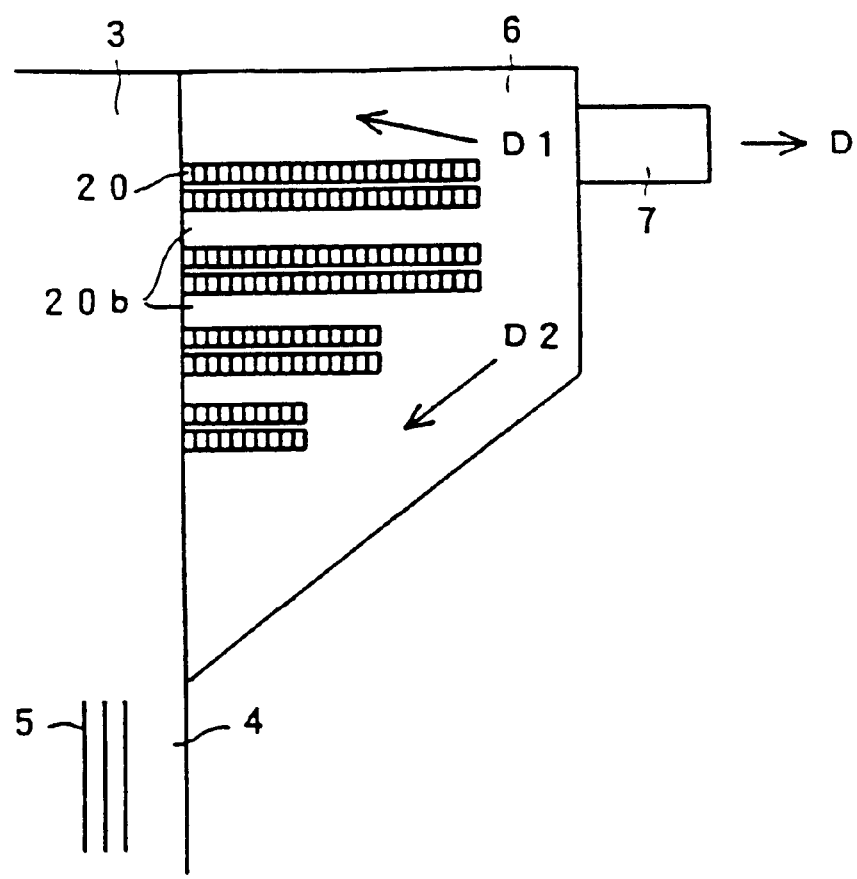
FIG. 5 is a stress relaxing structure in a second example included in a disposable diaper in accordance with the present invention.
Figure 6:
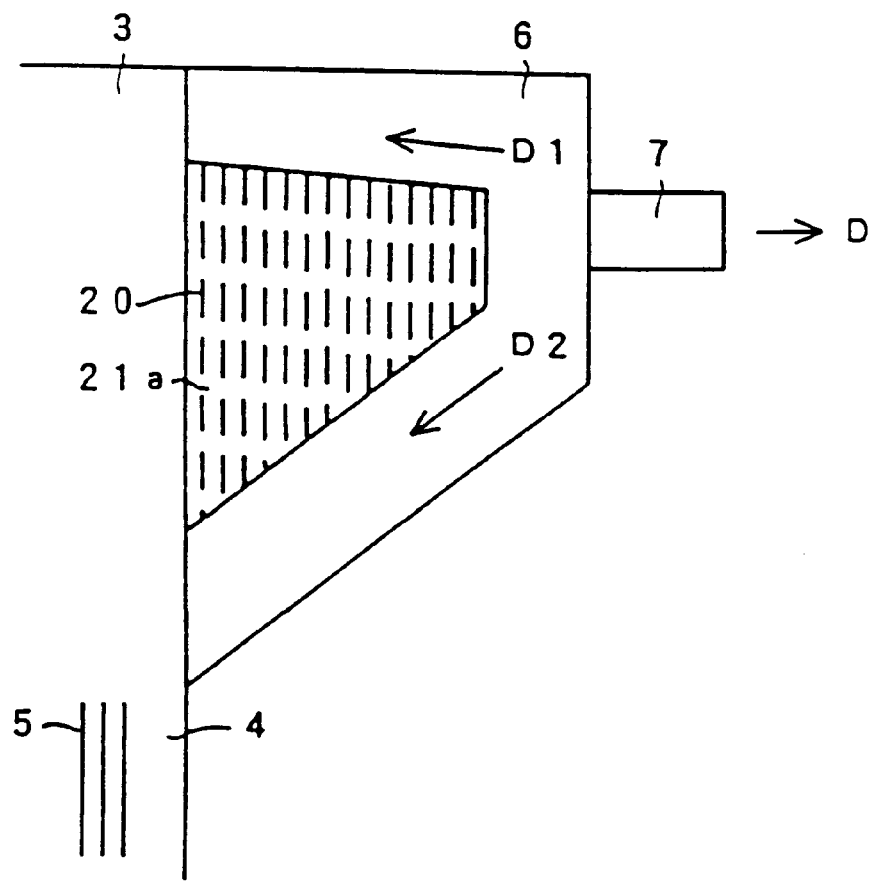
FIG. 6 is a stress relaxing structure in a third example included in a disposable diaper in accordance with the present invention.
Figure 7:
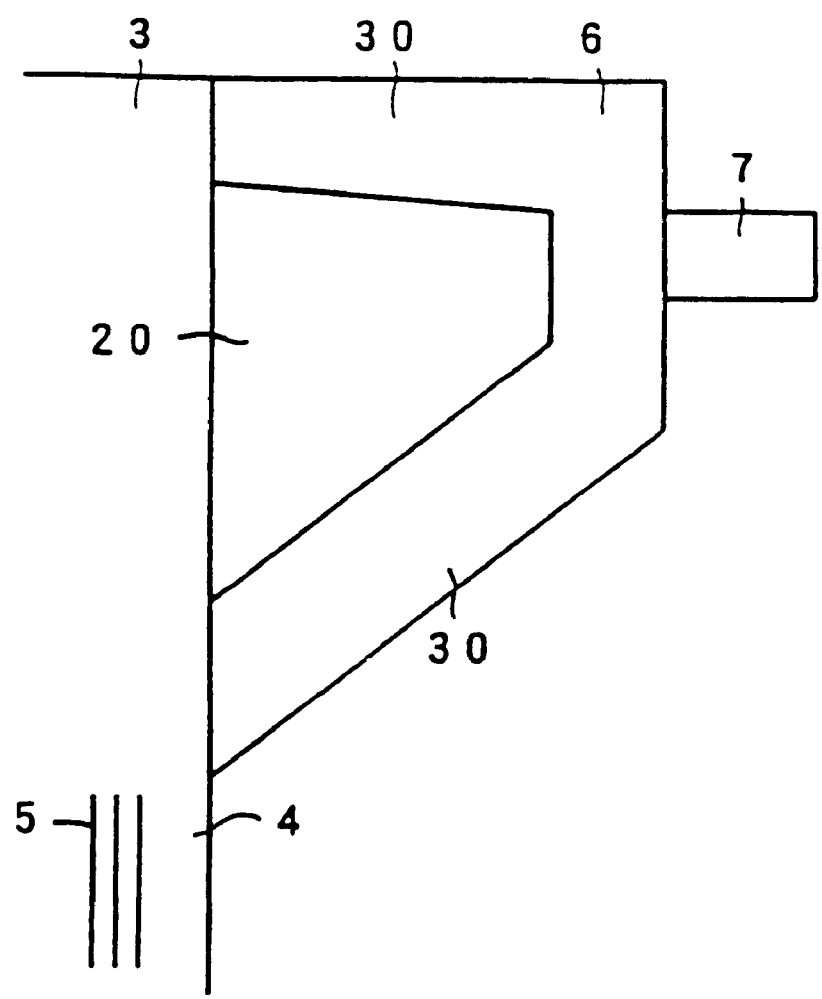
FIG. 7 is a stress relaxing structure in a fourth example included in a disposable diaper in accordance with the present invention.

As shown in FIG. 1, the ear parts 6 have each a stress relaxing structure 20 of a shape similar to that of the ear part 6 in their inner portions excluding the peripheral portions 6. As shown in FIG. 1, the stress relaxing structure 20 may be formed in a trapezoidal shape similar to and smaller than that of the ear part 6. The stress relaxing structure 20 may be formed in a substantially trapezoidal shape having longitudinal gaps 20a as shown in FIG. 4 or in a substantially trapezoidal shape having transverse gaps 20b as shown in FIG. 5. The stress relaxing structure 20 may be formed in any suitable shape other than a trapezoidal shape, such as a triangular shape, a rectangular shape, a shape of a part of an ellipse or a shape of a part of a circle, provided that the stress relaxing structure 20 has a function to relax stress. The stress relaxing structure 20 of the ear part 6 may be an aggregate of a plurality of longitudinal slits 21a formed in the laminated sheet forming the ear part 6 as shown in FIG. 6. The stress relaxing structure 20 may be a single slit 21a provided that the single slit 21a is capable of intercepting the transmission of a tensile force applied to the ear part 6 to the absorbent part 3. As shown in FIG. 7, the ear part 6 may be formed in an elastic structure, and a strip of an unstretchable film or an unstretchable strand 30 may be attached to a peripheral portion of the elastic structure excluding an inner trapezoidal elastic portion corresponding to the stress relaxing structure 20 to use the inner trapezoidal elastic portion as the stress relaxing structure 20.

When a tensile force is applied to the ear part 6, a tensile stress induced in the stress relaxing structure 20 is smaller than that which is induced in the peripheral portion of the ear part 6 surrounding the stress relaxing structure 20. Tensile stress is a resistive force developed by a material bearing a tensile load. Therefore, "a structure having a small tensile stress" is a structure yielding to and easily stretchable by a comparatively small tensile force. Structures expressed by the term "stress relaxing structure" include a vacancy formed in the ear part 6 and virtually serving as a stress relaxing structure 20.

Figure 8:
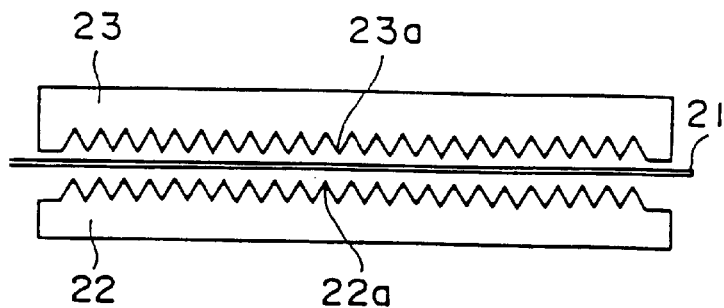
FIG. 8 is a typical side view of assistance in explaining a stress relaxing structure forming device.
Figure 9:
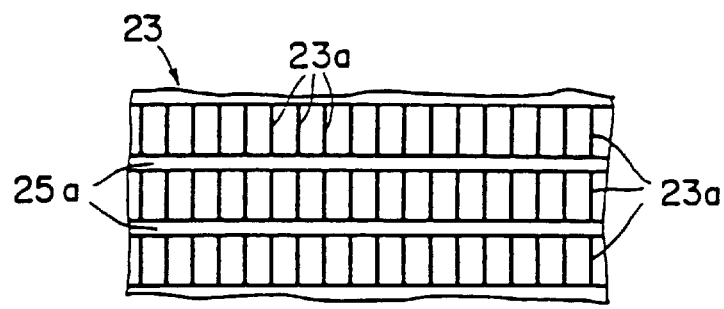
FIG. 9 is a plan view of a forming plate of the stress relaxing structure forming device.
Figure 10:
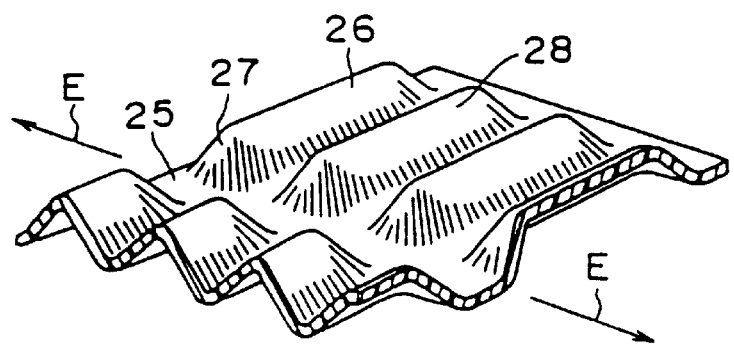
FIG. 10 is a fragmentary perspective view of a stress relaxing structure formed by the stress relaxing structure forming device of FIG. 8.

Preferably, the stress relaxing structure 20 is formed by the following method. As shown in FIG. 8, a sheet 21 to form the ear part 6 is compressed between a plate 22 provided with a plurality of ridges 22a in an area of the inner surface thereof corresponding to the stress relaxing structure 20, and a plate 23 provided with a plurality of ridges 23a in an area of the inner surface thereof corresponding to the stress relaxing structure 20. As shown in FIG. 9, narrow grooves 25a are formed across the plurality of ridges 23a of the plate 23. The plurality of ridges 22a of the plate 22 are continuous and not interrupted. As shown in FIG. 10, the stress relaxing structure 20 formed by thus compressing the sheet 21 between the plates 22 and 23 has a plurality of undeformed sections 25, a plurality of permanently deformed sections 26, and transitional sections 27 between the undeformed sections 25 and the permanently deformed sections 26. Ridges 28 are formed in the permanently deformed sections 26. The undeformed sections 25 are defined by the narrow grooves 25a of the plate 23 and the corresponding portions of the ridges 22a of the plate 22, and the permanently deformed sections 26 are defined by the respective ridges 22a and 23a of the plate 22 and the plate 23.

Figure 11:
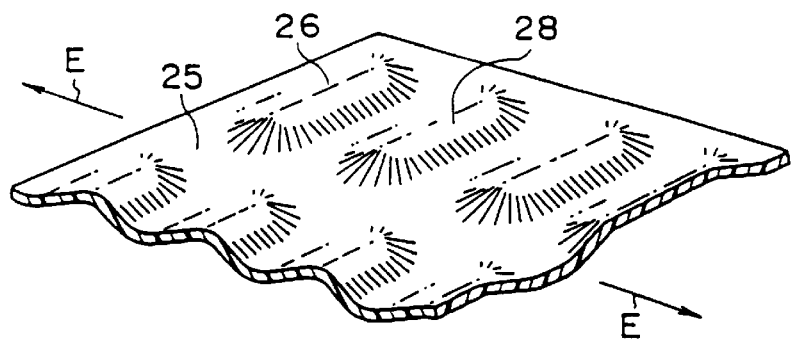
FIG. 11 is a fragmentary perspective view of a formed intermediate film shown in FIG. 10, in a half stretched state.
Figure 12:
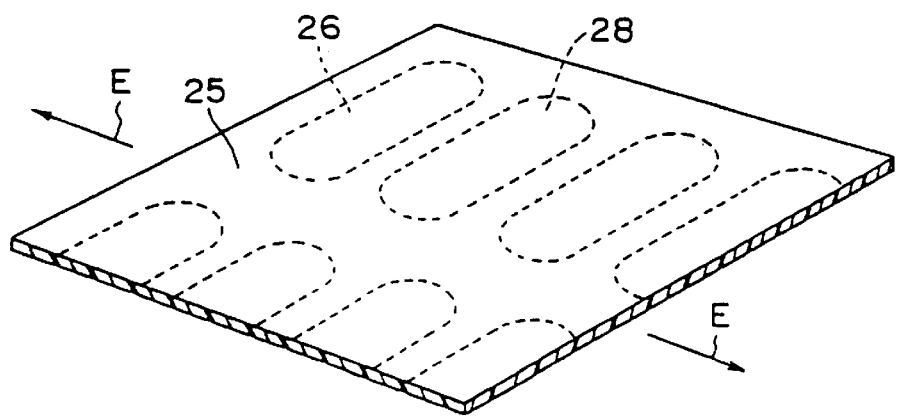
FIG. 12 is a fragmentary perspective view of the formed intermediate film shown in FIG. 10 in a fully stretched state.

When the ear part 6 is tensioned by forces acting in the directions of the arrows E as shown in FIG. 10, the undeformed sections 25 are plastically stretched to some extent as shown in FIG. 11 and, as the undeformed sections 25 are further stretched, the ridges 28 of the permanently deformed sections 26 are flattened as shown in FIG. 12 and the ear part 6 cannot be stretched any further. When the sheet 21 having such characteristics is a laminated sheet, at least one of the component layer of the sheet 21 is formed of a stretchable film, such as a polyolefin film, a low-density linear polyethylene film, a low-density polyethylene film, a high-density polyethylene film or a polypropylene film.

The stress relaxing structure 20 that can be stretched by a small tensile force is thus formed in the sheet 21 forming the ear part 6. Since the periphery of the sheet 21 surrounding the stress relaxing structure 20 is unprocessed, the periphery of the sheet 21 does not yield to tension when the sheet 21 is tensioned or the periphery is harder to stretch than the stress relaxing structure 20. When tensioned, the stress relaxing structure 20 yields to the tensile force to absorb the tensile force and does not cause the peripheral portion of the ear part 6 to shrink.

The sheet 21 forming the ear part 6 may be formed of a somewhat stretchable material. When formed of such a somewhat stretchable material, the stress relaxing structure 20 can be formed in the sheet 21 by the aforesaid process. In either case, the stress relaxing structure 20 can be stretched by a tensile force smaller than that necessary for stretching the peripheral portion of the ear part 6.

Figure 13:
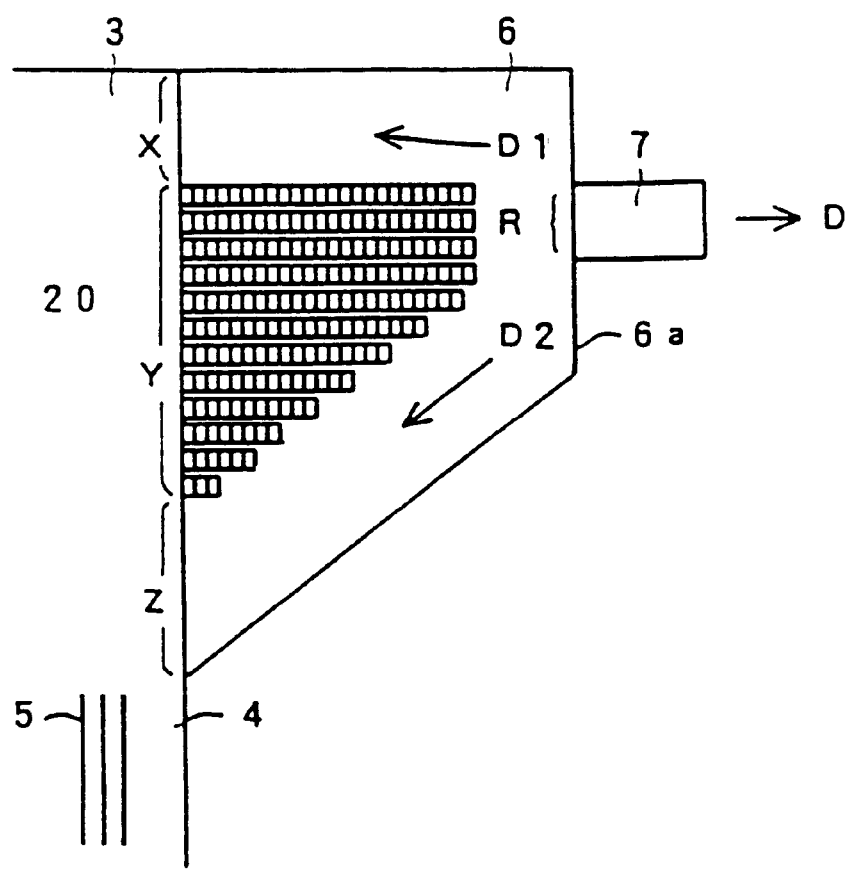
FIG. 13 is a fragmentary development of a disposable diaper in accordance with the present invention, of assistance in explaining the substantially equal distribution of a tensile force applied to a fastener to a waist lapping section and a leg lapping section.

As shown in FIG. 13, when a tensile force D is applied to the fastener 7 in a direction perpendicular to the side edge 6a of the ear part 6, the stress relaxing structure 20 of the ear part 6 serves to divide the tensile force D into a component tensile force D1 acting on the waist lapping portion and a component tensile force D2 acting on the leg lapping portion. That is, since a tensile force greater than that necessary for stretching the stress relaxing structure 20 must be applied to the peripheral portions of the ear part 6 to stretch the peripheral portion, most part of the tensile force D applied to the fastener 7 is divided into the component tensile forces D1 and D2, and the component tensile forces D1 and D2 act directly on regions X and Z of the absorbent part 3, respectively. Even if part of the tensile force D acts on the stress relaxing structure 20, the stress relaxing structure 20 is not stretched in a extreme state as shown in FIG. 12 because the stress relaxing structure 20 can be stretched by a comparatively small tensile force and the peripheral portion surrounding the stress relaxing structure 20 cannot be virtually stretched. Thus, the stretchable stress relaxing structure 20 absorbs the tensile force that acts thereon and, consequently, any tensile force is not transmitted directly to a region Y of the absorbent part 3. Thus the tensile force D applied to the fastener 7 is divided into the component tensile force D1 acting on the waist lapping portion of the absorbent part 3 and the component tensile force D2 acting on the leg lapping portion of the absorbent part 3 to fasten the absorbent part 3 around the waist and the leg.

Figure 14:
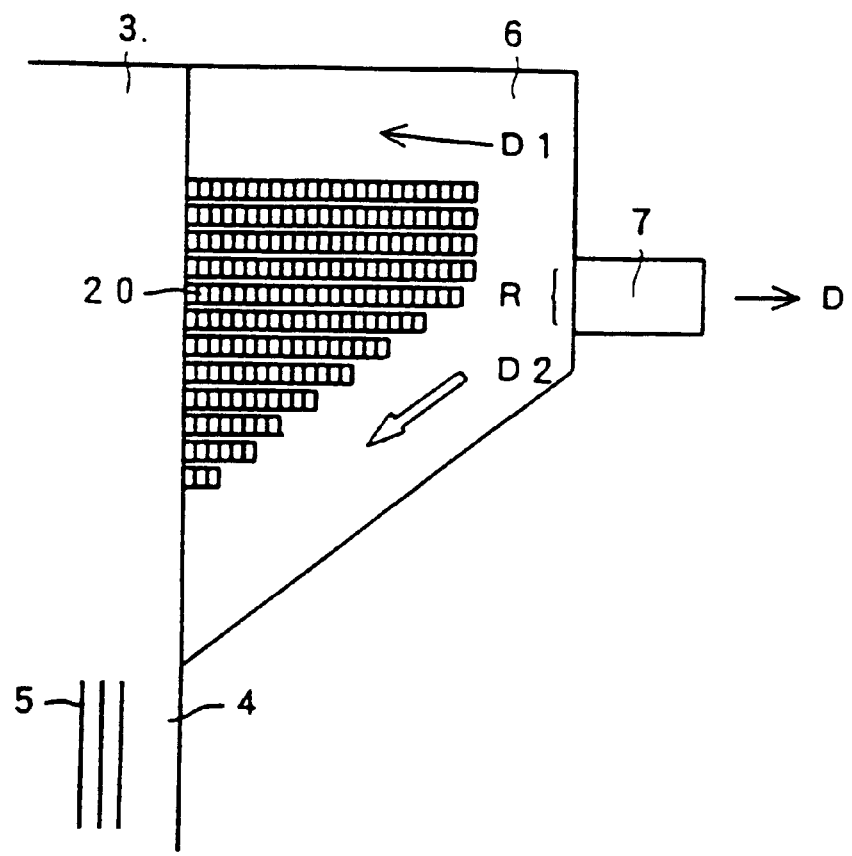
FIG. 14 is a fragmentary development of a disposable diaper in accordance with the present invention, of assistance in explaining the distribution of a major part and a minor part of a tensile force applied to a fastener to a waist lapping section and a leg lapping section, respectively, of the disposable diaper.
Figure 15:
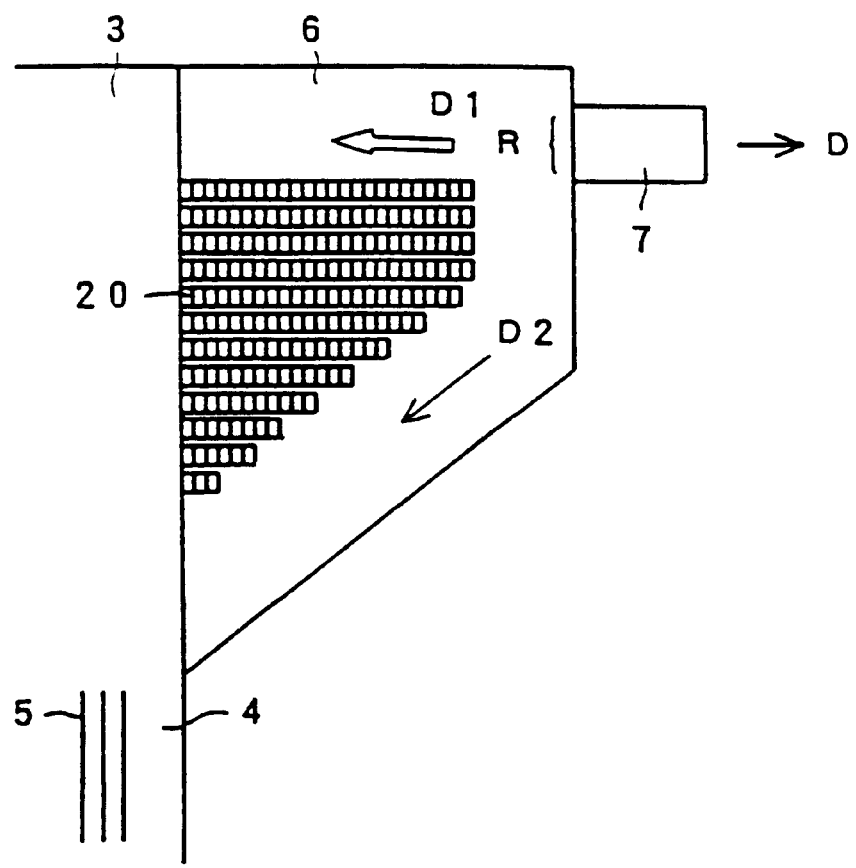
FIG. 15 is a fragmentary development of a disposable diaper in accordance with the present invention, of assistance in explaining the distribution of a minor part and a major part of a tensile force applied to a fastener to a waist lapping section and a leg lapping section, respectively, of the disposable diaper.

The division of the tensile force D applied to the fastener 7 into the component tensile forces D1 and D2 cam be adjusted by adjusting the position of a pulling section R where the fastener 7 is attached to the oblique side edge 6a of the ear part 6. When the pulling section R corresponds substantially to the middle of the side edge of the stress relaxing structure 20 as shown in FIG. 13, the tensile force D applied to the fastener 7 in the direction of the arrow is divided into the component tensile force D1 acting around the waist and the tensile force D2 acting around the leg, and the component tensile forces D1 and D2 are substantially equal to each other. When the pulling section R is at a position shown in FIG. 14 below the position of the pulling section R shown in FIG. 13, the tensile force D applied to the fastener 7 in the direction of the arrow is divided into the component tensile forces D1 and D2, the component tensile force D1 that acts around the waist is comparatively small and the component tensile force D2 that acts around the leg is comparatively large. When the pulling section R is at a position shown in FIG. 15 above the position of the pulling section R shown in FIG. 13, the tensile force D applied to the fastener 7 in the direction of the arrow is divided into the component tensile forces D1 and D2, the component tensile force D1 that acts around the waist is comparatively large and the component tensile force D2 that acts around the leg is comparatively small.

Figure 16:
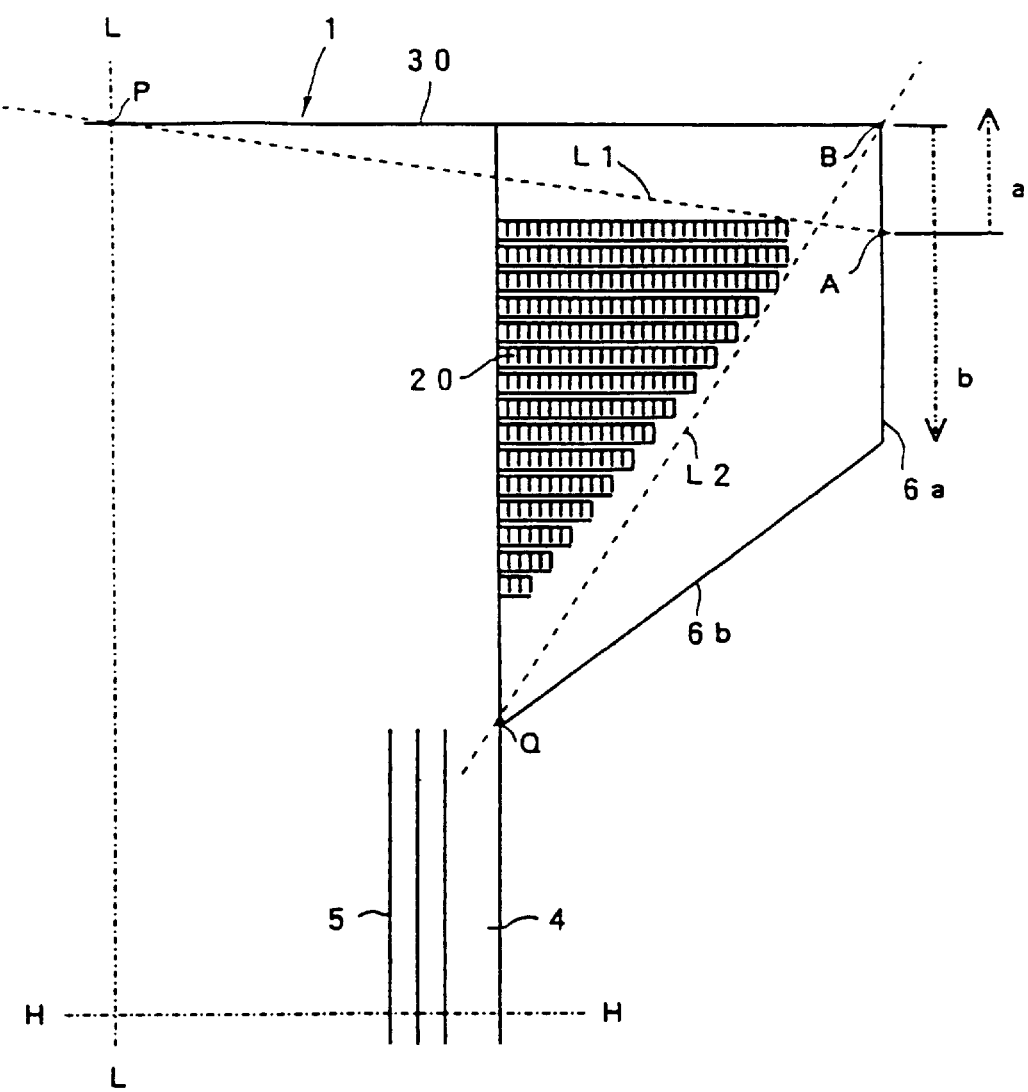
FIG. 16 is a fragmentary development of assistance in explaining a first side edge section a and a second side edge section b.

The position of the pulling section R and the position a1 relation between the same and other parts to distribute the tensile force applied to the fastener 7 surely to desired portions of the absorbent part 3 will be described below. The position of the pulling section R for the fastener 7 on the oblique side edge 6a is determined by construction shown in FIG. 16. The position of the pulling section R is important for effectively and directly distributing a tensile force applied to the fastener 7 to a desired waist lapping portion and a desired leg lapping portion of the disposable diaper 1. Referring to FIG. 16, a line L-L' indicates the longitudinal center axis of the disposable diaper 1 (absorbent part 3) and a line H-H' indicates the transverse center axis of the disposable diaper 1 (absorbent part 3) perpendicular to the longitudinal center axis L-L'. Indicated at P is the intersection point of the longitudinal center axis L-L' and the upper edge 1a of the first waist lapping section 2a, at Q is the intersection point of the lower edge 6b of the ear part 6 on the side of the transverse center axis H-H' and the side flap 4) at L1 is a first boundary line extending from the intersection point P so as to be tangent to a point on the stress relaxing structure 20 on the side of the upper edge 1a, at L2 is a second boundary line extending from the intersection point Q so as to be tangent to a point on the stress relaxing structure 20 on the side of the transverse center axis H-H', at A is the intersection point of the first boundary line L1 and the side edge 6a, and at B is the intersection point of the second boundary line L2 and the side edge 6a. A first side edge section a extends on the side of the upper edge 1a from the intersection point A, and a second side edge section b extends on the side of the transverse center axis H-H' from the intersection point B.

Figure 17:
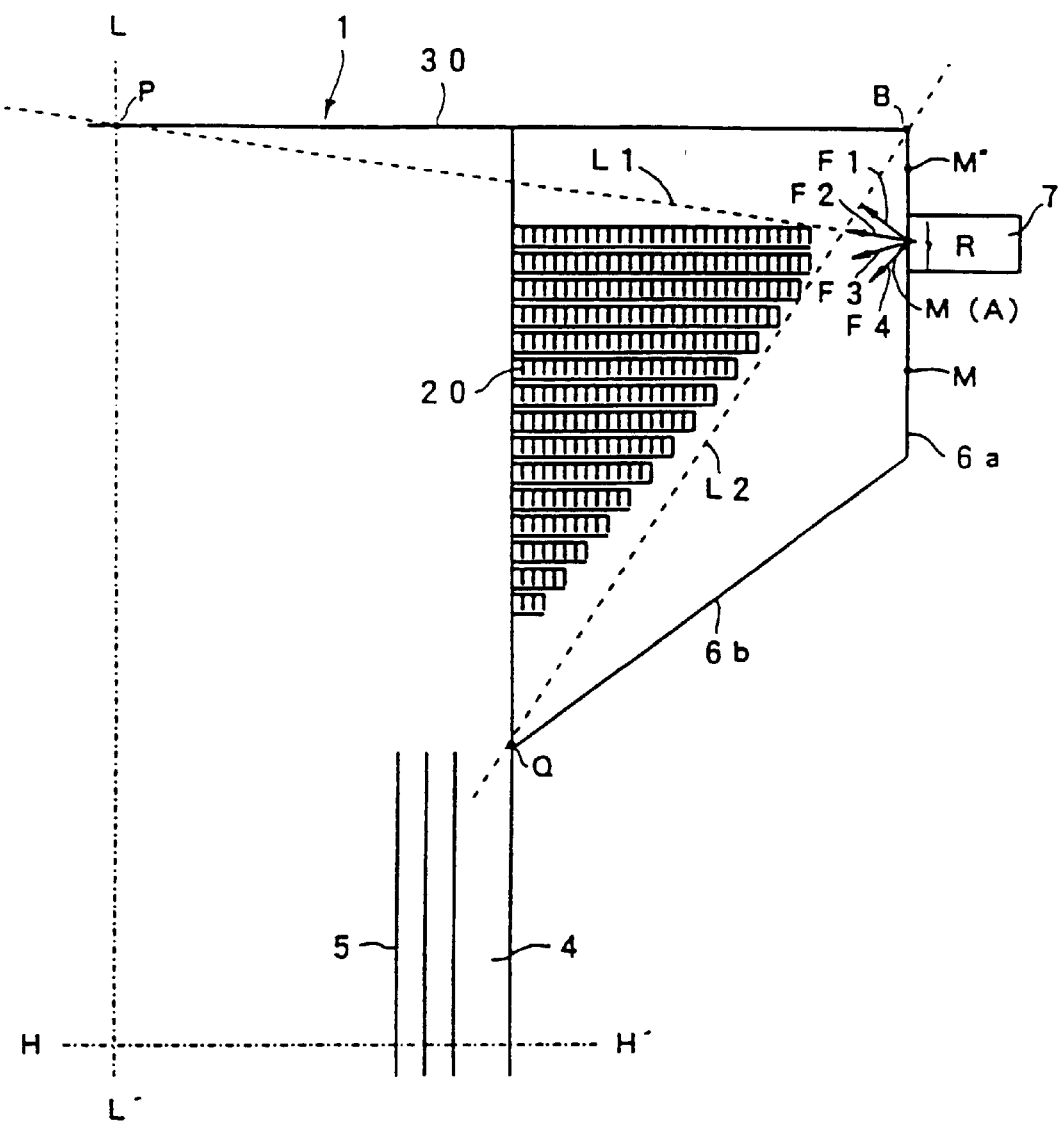
FIG. 17 is a fragmentary development of assistance in explaining the distribution of a tensile force applied to the fastening means.

A tensile force D applied to the side edge 6a by the fastener 7 is distributed in the ear part 6 as shown in FIG. 17. In FIG. 17, a point M of action of the tensile force applied to the fastener 7 is in the pulling section R in which the fastener 7 is attached to the side edge 6a and coincides with the intersection point A in this example. When part of a tensile force applied to the fastener 7 acts on the side edge 6a at the point M of action, the part of the tensile force is decomposed into representative component forces F1, F2, F3 and F4. The component force F1 is directed toward the upper edge 1a and not directly toward the intersection point P. Therefore, the component force F1 does not act directly on the intersection point P. The direction of the component force F2 is aligned with the first boundary line L1 and hence the component force F2 acts directly on the intersection point P. The component force F3 is directed toward the stress relaxing structure 20 and tends to stretch the stress relaxing construction 20. However, since the stress relaxing structure 20 absorbs the force applied thereto, the component force F3 is not transmitted to the region Y of the absorbent part 3 shown in FIG. 13. The component force F4 is directed toward the intersection point Q and acts directly on the absorbent part 3 at the intersection point Q.

If the point M of action in the pulling section R in which the fastener 7 is attached to the side edge 6a is on the side of the transverse center axis H-H' with respect to the intersection point A, i.e., at a point M' outside the first side edge section a (FIG. 16), the component force F2 directed from the point M' toward the intersection point P is absorbed by the stress relaxing structure 20 and is ineffective. Therefore, no component force acts directly on the intersection point P if the point M of action of the tensile force applied to the fastener 7 on the side edge 6a is at the point M'. If the point M action is shifted to a point M" on the side of the upper edge 1a with respect to the intersection point A shown in FIG. 17, i.e., if the point M of action is in the first side edge section a, some component force acts directly on the intersection point P.

As is obvious from the foregoing explanation, the first boundary line L1 is a boundary line between positions for the point M of action that enables the direct action of a component force of the tensile force applied to the fastener 7 on the intersection point P and those for the point M of action that disables the direct action of the component force on the intersection point P. When the point M of action at which the tensile force applied to the fastener 7 acts on the ear part 6 is in the first side edge section a, at least part of the tensile force applied to the point M of action is able to act directly on the intersection point P. The second boundary line L2 drawn in connection with the intersection point Q is a boundary line between positions for the point M of action that enables the direct action of a component force of the tensile force applied to the fastener 7 on the intersection point Q. When the point M of action at which the tensile force applied to the fastener 7 acts on the ear part 6 is in the second side edge section b, at least part of the tensile force applied to the point M of action is able to act directly on the intersection point Q. Accordingly, part of the tensile force applied to the fastener 7 can be applied directly on the desired points P and Q on the absorbent part 3 when the pulling section R in which the fastener 7 is attached to the side edge 6a of the ear part 6 overlaps part of the first side edge section a defined by the first boundary line L1 and part of the second side edge section b defined by the second boundary line L2. Since the intersection point P is on the longitudinal center axis L-L' of the disposable diaper 1, the waist lapping portion of the disposable diaper 1 can be firmly fastened around the waist by applying tensile forces to the two ear parts 6, when part of each of the tensile forces can be applied directly to the intersection point P. When part of the tensile force applied to each fastener 7 can be directly applied to the intersection point Q, the leg lapping portion of the absorbent part 3 can be firmly fastened around the leg.

Figure 18:
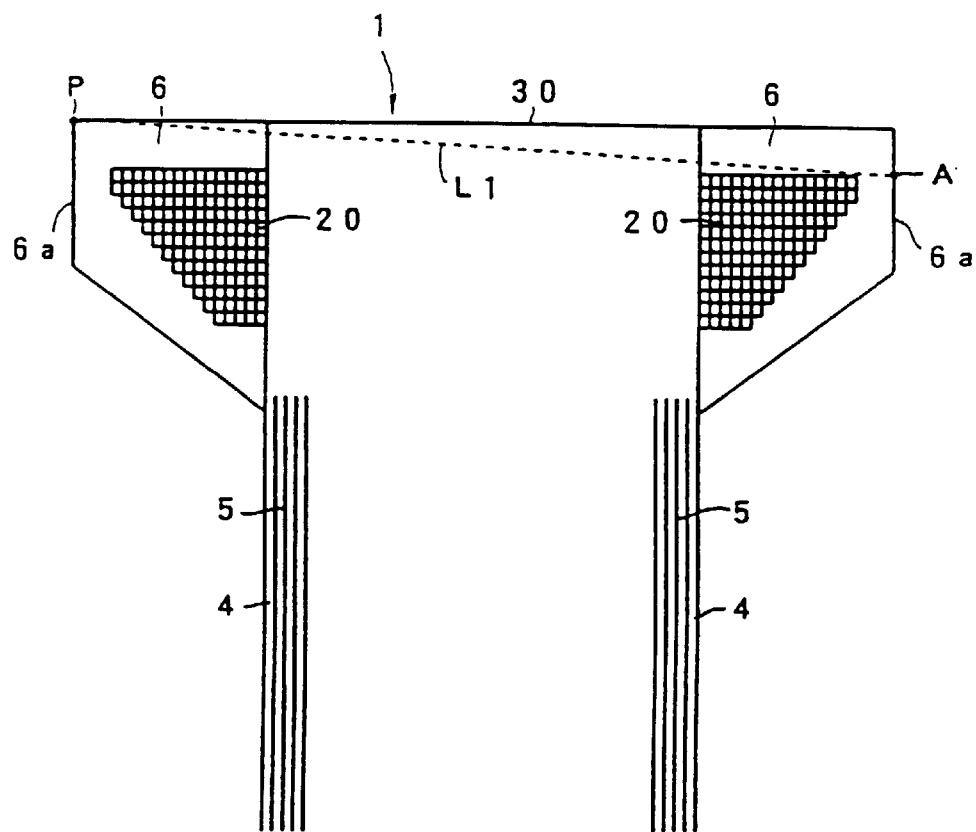
FIG. 18 is a fragmentary development of assistance in explaining a method of determining a first side edge section.
Figure 19:
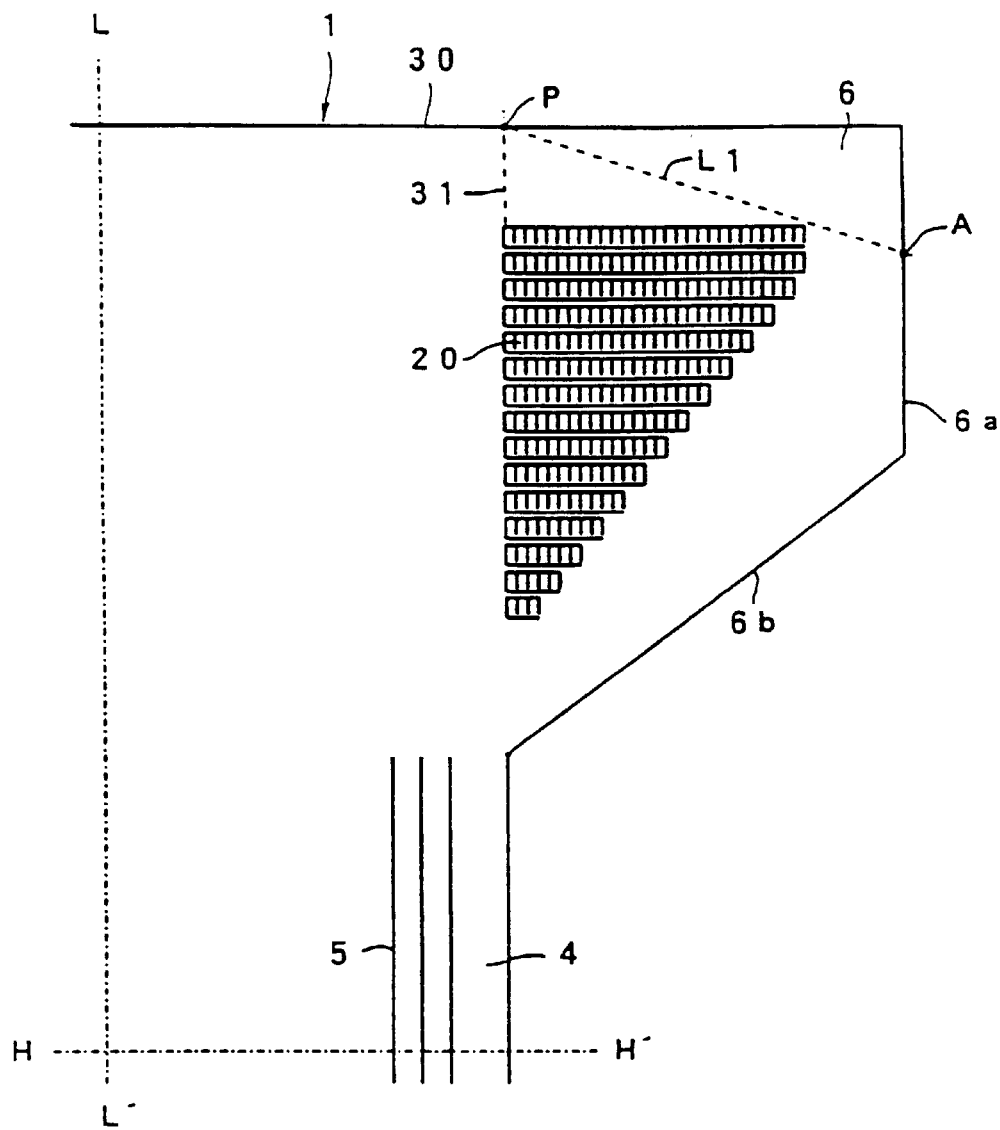
FIG. 19 is a fragmentary development of assistance in explaining another method of determining a first side edge section.

In a disposable diaper 1 in a second embodiment according to the present invention, a first boundary line L1 may be extended from the intersection point P of the leftward extension of the upper edge 1a of an absorbent part 3 and the side edge 6a of a left ear part 6 as shown in FIG. 18. A first boundary line L1 may be extended from the intersection point P of a line extending along the inner side of a stress relaxing structure 20 in parallel to the longitudinal center axis L-L' of an absorbent part 3 and the upper end edge 1a of the absorbent part 3 as shown in FIG. 19. In either case, the first boundary line L1 is extended from the intersection point P in tangent to an upper point on the stress relaxing structure 20, to determine an inter section point A on the side edge 6a of a right ear part 6.

The respective magnitudes of a component tensile force D1 for fastening the waist lapping portion of the absorbent part 3 around the waist and a component tensile force D2 for fastening the leg lapping portion of the absorbent part 3 around the leg are determined by adjusting the ratio of the size of a portion of the pulling section R, in which a fastener 7 is attached to the side edge 6a, overlapping the first side edge section a to the size of the pulling section R, and the ratio of the size of a portion of the pulling section R overlapping the second side edge section b to the size of the pulling section R. The greater the portion of the pulling section R, overlapping the first side edge section a, the greater is the ratio of the component tensile force D1 that acts on the intersection point P to the tensile force applied to the fastener 7. An area defined by the first boundary line L1, the upper edge of the ear part 6 and a portion of the side edge 6a of the ear part 6 extending upward from the intersection point A is a waist lapping portion fastening component force distributing area 42, and a portion of the side edge 6a associated with the waist lapping portion fastening component force distributing area 42 is a first side edge section a. As long as part of the pulling section R in which the fastener 7 is attached to the side edge 6a overlaps the first side edge section a, a component tensile force of the tensile force applied to the fastener 7 acts directly on the intersection point P. The greater the portion of the pulling section R, overlapping the first side edge section a, the greater is the component tensile force D1 distributed to the waist lapping portion fastening component force distributing area 42.

On the other hand, the greater the portion of the pulling section R, overlapping the second side edge section b, the greater is the component tensile force D2 that acts directly on the intersection point Q. An area defined by the second boundary line L2, the lower side edge 6b of the ear part 6 and a portion of the side edge 6a of the ear part 6 extending downward from the intersection point B is a leg lapping portion fastening component force distributing area 43, and a portion of the side edge 6a associated with the leg lapping portion fastening component force distributing area 43 is a second side edge section b. As long as part of the pulling section R overlaps the second side edge section b, a component tensile force of the tensile force applied to the fastener 7 acts directly on the intersection point Q. The greater the portion of the pulling section R, overlap ping the second side edge section b, the greater is the component tensile force D2 distributed to the leg lapping portion fastening component force distributing area 43.

Figure 20:
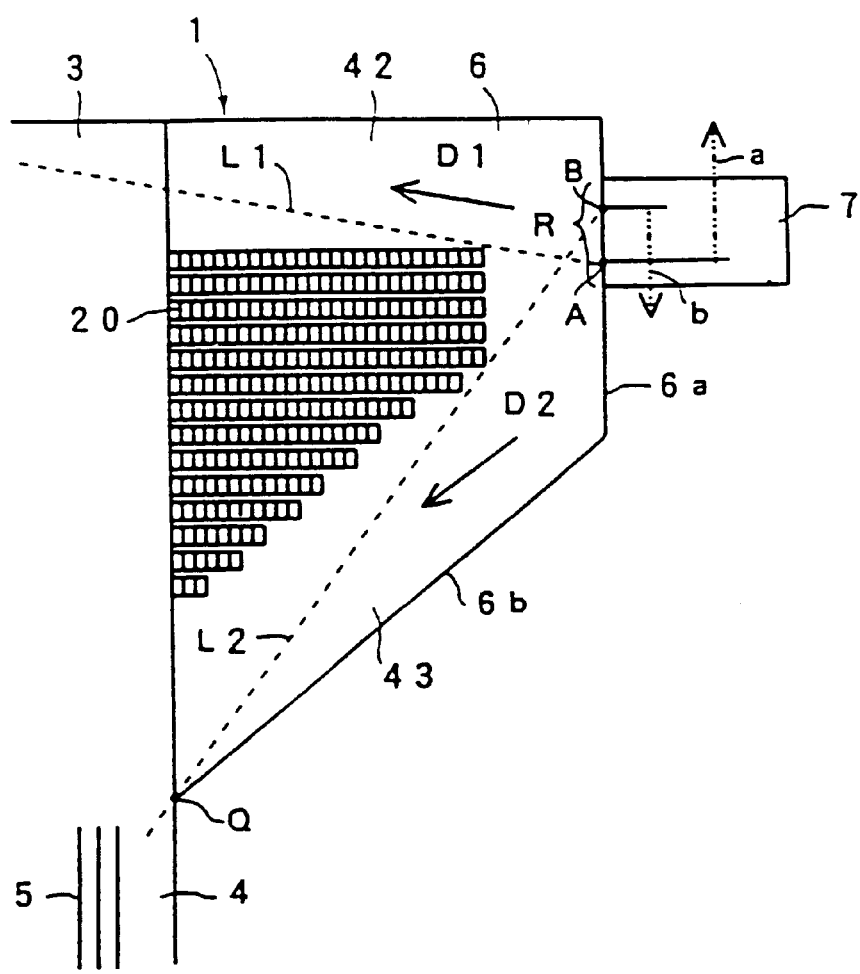
FIG. 20 is a fragmentary development showing a fastening means attached to an ear part in a pulling section equally overlapping a first side edge section a and a second side edge section b.
Figure 21:
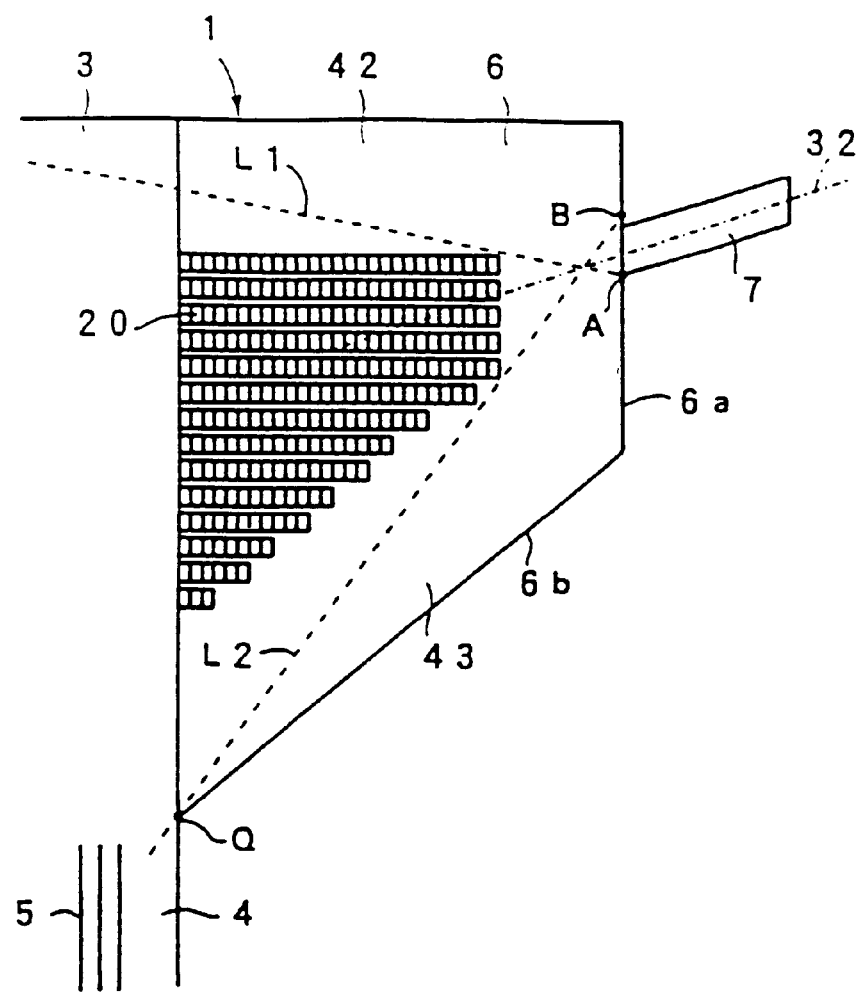
FIG. 21 is a fragmentary development showing a fastening means attached to an ear part in a pulling section with its longitudinal axis aligned with the bisector of the angle between a first boundary line and a second boundary line.

When the pulling section R, in which the fastener 7 is attached to the ear part, includes the intersection points A and B, and the intersection points A and B are at equal distances from the bisector of the pulling section R as shown in FIG. 20, a portion of the pulling section R over lapping the first side edge section a and a portion of the pulling section R overlapping the second side edge section b are substantially equal to each other. Therefore, the component tensile forces D1 and D2 distributed to the waist lapping portion fastening component force distributing area 42 and the leg lapping portion fastening component force distributing area 43 are substantially equal to each other, and hence substantially equal tensile forces are applied to the intersection points P and Q, respectively. When the fastener 7 is attached to the ear part 7 with its longitudinal axis aligned with the bisector of the angle between the first boundary line L1 and the second boundary line L2 as shown in FIG. 21, the tensile force can be further equally distributed to the component force distributing areas 42 and 43.

Figure 22:
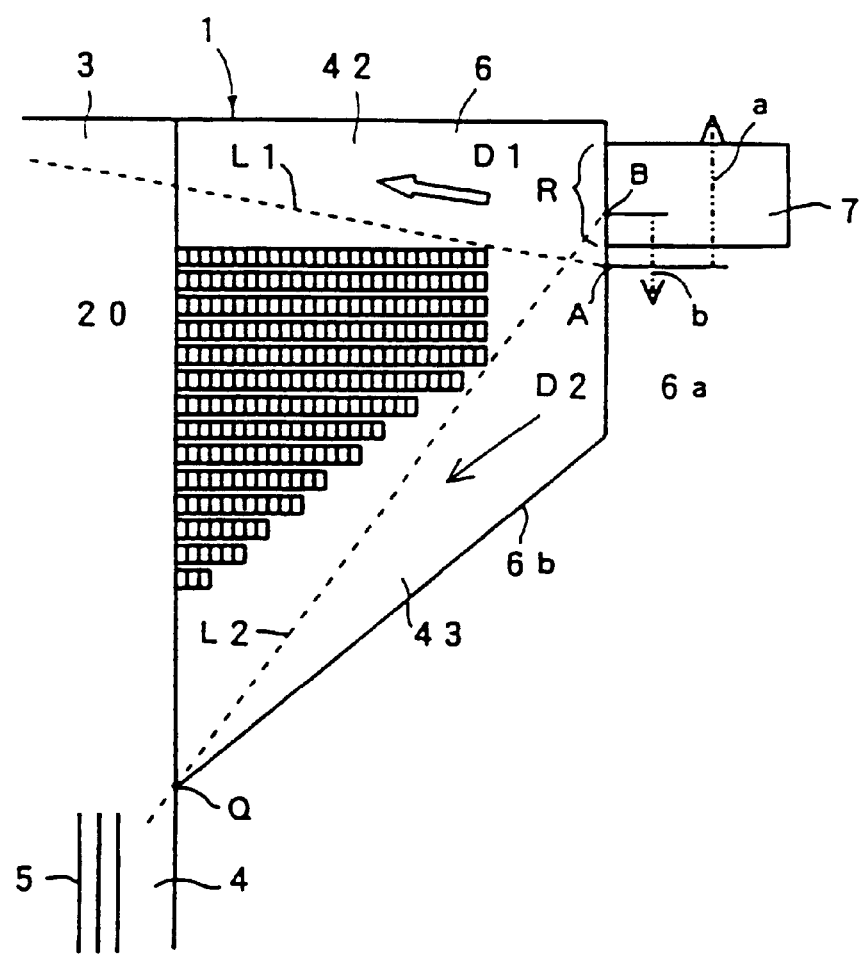
Figure 23:
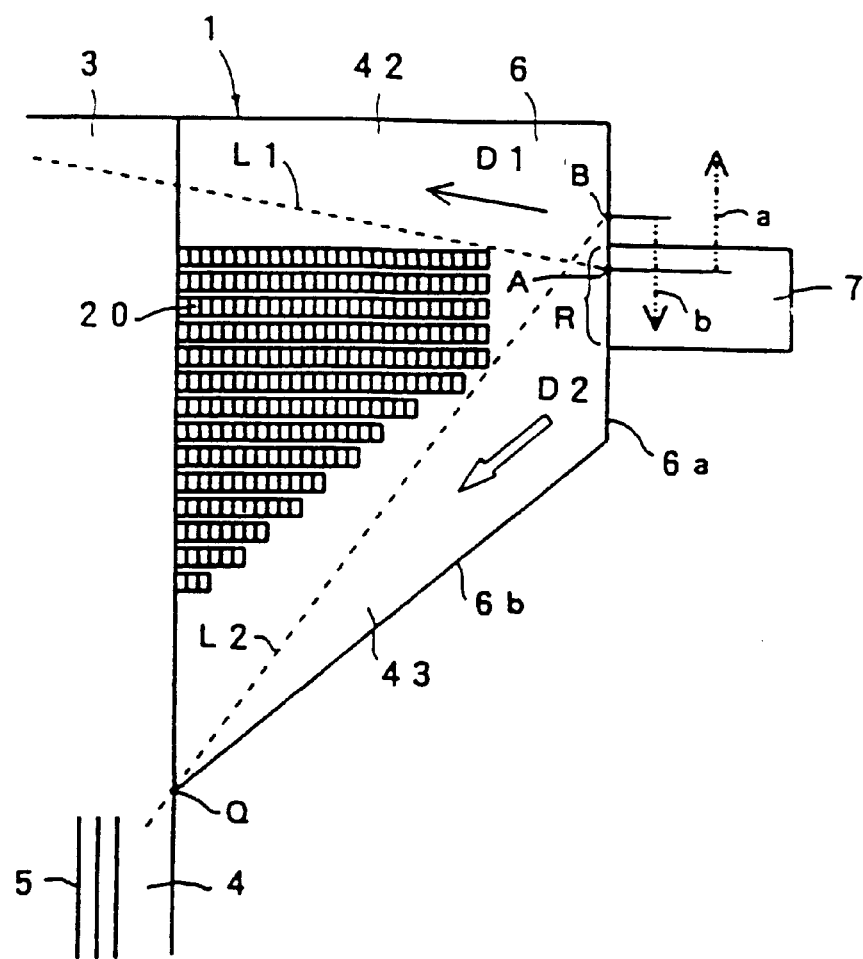

The ratio between the component tensile force D1 distributed to the waist lapping portion fastening component force distributing area 42 and the component tensile force D2 distributed to the leg lapping portion fastening component force distributing area 43 can be adjusted by adjusting the ratio of the size of a portion of the pulling section R, in which a fastener 7 is attached to the side edge 6*a*, overlapping the first side edge section a to the size of the pulling section R, and the ratio of the size of a portion of the pulling section R overlapping the second side edge section b to the size of the pulling section R. When the pulling section R overlaps the first side edge section a entirely and overlaps the second side edge section b partly as shown in FIG. 22, a major part of the tensile force applied to the fastener 7 is distributed to the waist lapping portion fastening component force distributing area 42. When the pulling section R overlaps the second side edge section b entirely and overlaps the first side edge section a partly as shown in FIG. 23, a major part of the tensile force applied to the fastener 7 is distributed to the leg lapping portion fastening component force distributing area 43. The pulling section R need not necessarily be included in either the first side edge section a or the second side edge section b, provided that pulling section R overlaps the first side edge section a and the second side edge section b at different overlapping ratios, respectively.

Figure 24:
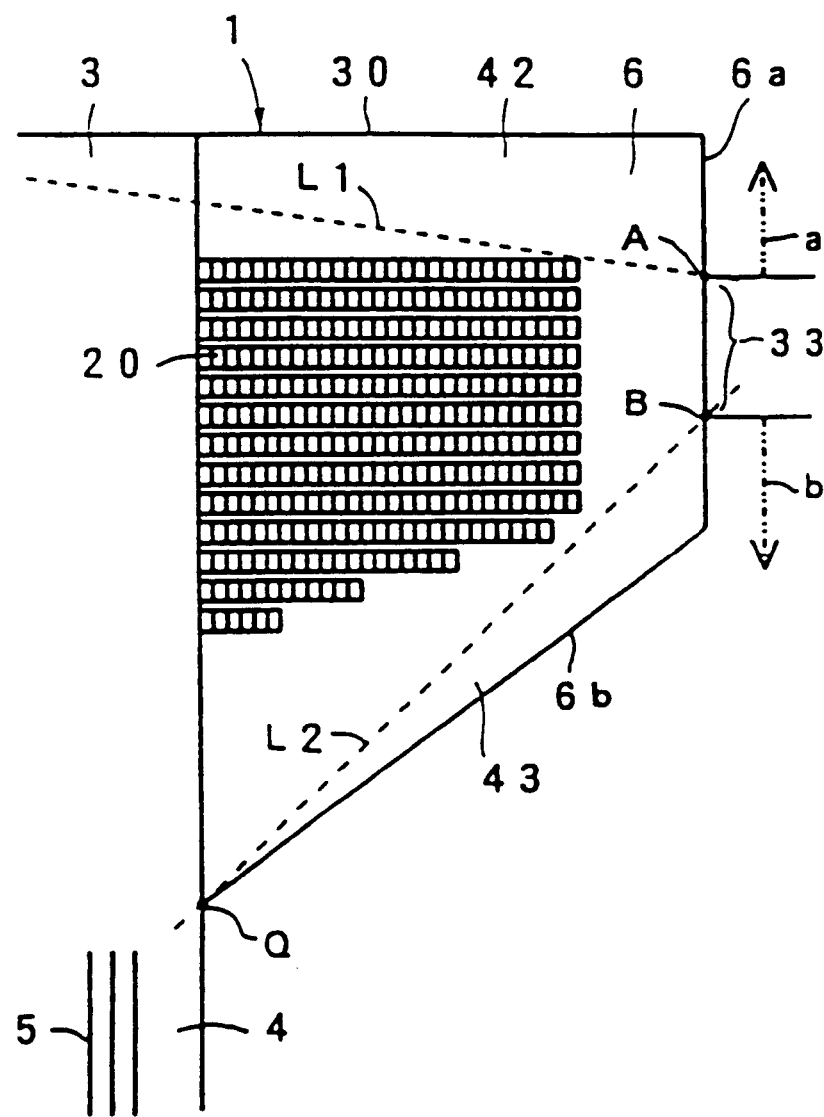
FIG. 24 is a fragmentary development of assistance in explaining the relation between a stress relaxing structure, and a first side edge section a and a second side edge section b.
Figure 25:
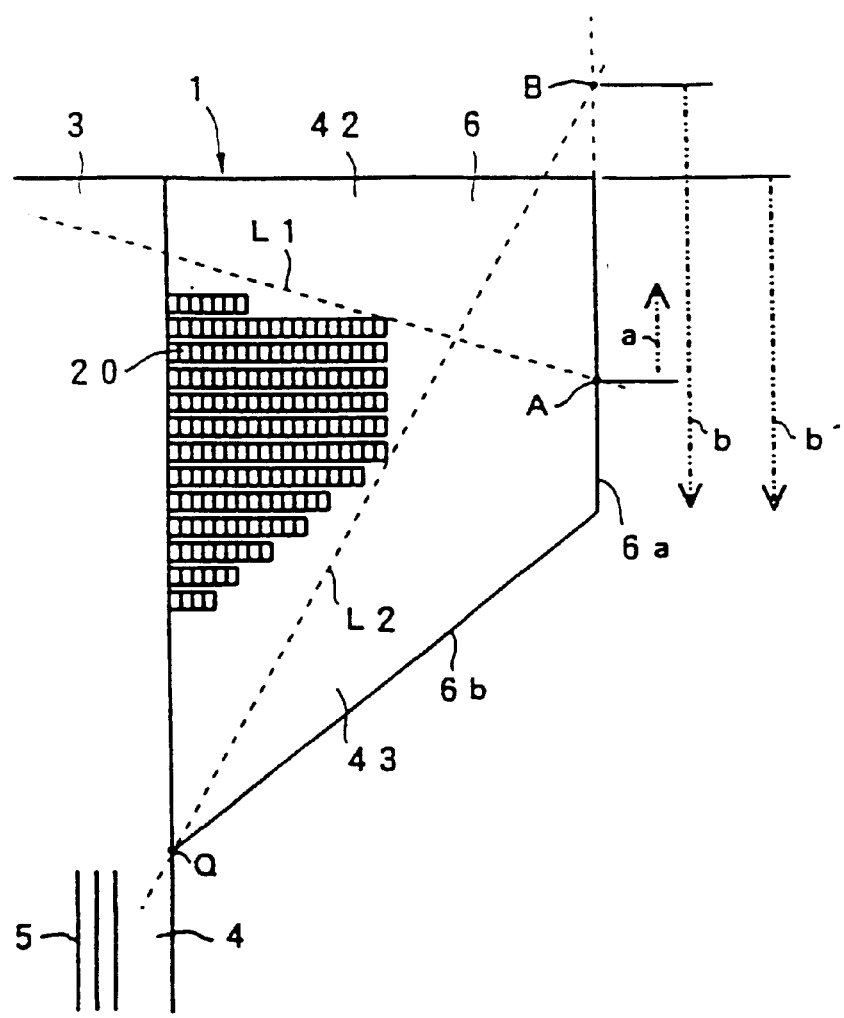
FIG. 25 is a fragmentary development of assistance in explaining the relation between a stress relaxing structure, and a first side edge section a and a second side edge section b.

FIGS. 24 and 25 show the dependence of the relation between the first side edge section a and the second side edge section b on the position of a stress relaxing structure 20 in an ear part 6 in a disposable diaper 1 in a third embodiment according to the present invention. Referring to FIG. 24, the stress relaxing structure 20 has a shape resembling a rectangle, which is different from the shape of the stress relaxing structure 20 shown in FIG. 16. In the third embodiment, the first boundary line L1 extending from the intersection point P so as to be tangent to the stress relaxing structure 20 and the second boundary line L2 extending from the intersection point Q so as to be tangent to the stress relaxing structure 20 do not intersect each other within the ear part 6. The lines L1 and L2 intersect the side edge 6*a* at intersection points A and B, respectively. A first side edge section a extends on the side of the upper edge 1*a* of an absorbent part 3 from the intersection point A, a second side edge section b extends on the side of the transverse center axis H-H' of the absorbent part 3 from the intersection point B, and a neutral section 33 connected with neither the waist lapping portion fastening component force distributing area 42 nor the leg portion fastening component force distributing area 43 is formed between the first side edge section a and the second side edge section b. The pulling section R in which a fastener 7 is attached to the side edge 6*a* must extend across the neutral section 33 and overlap the side edge sections a and b partly to concentrate the component forces of the tensile force applied to the fastener 7 directly on the waist lapping portion and the leg lapping portion; that is, the component forces of the tensile force applied to the fastener 7 can be directly concentrated on desired portions by determining the position of the pulling section R so that the pulling section R overlap the side edge sections a and b partly.

In a disposable diaper 1 in a fourth embodiment according to the present invention shown in FIG. 25, a first boundary line L1 is extended from the intersection point P so as to be tangent to a stress relaxing structure 20 and intersects the side edge 6*a* of an ear part 6 at an intersection point A, and a second boundary line L2 is extended from the intersection point Q so as to be tangent to the stress relaxing structure 20 and intersects an extension of the side edge 6*a* at an intersection point B. Since the inter section point B is a virtual point apart from the ear part 6, an actual second side edge section b' is a portion of a second side edge section b, on the side edge 6*a*. A fastener 7 is attached to the side edge 6*a* in a pulling section R partially overlapping the first side edge section a and the actual second side edge section b'. Thus the side edge sections a and b can be defined even if the lines L1 and L2 do not intersect the side edge 6*a*. In this specification, an expression, "a point where the first boundary line L1 (second boundary line L2) intersects the side edge 6*a*" has an implication that "a point where the first boundary line L1 (second boundary line L2) intersects an extension of the side edge 6*a*".

Figure 26:
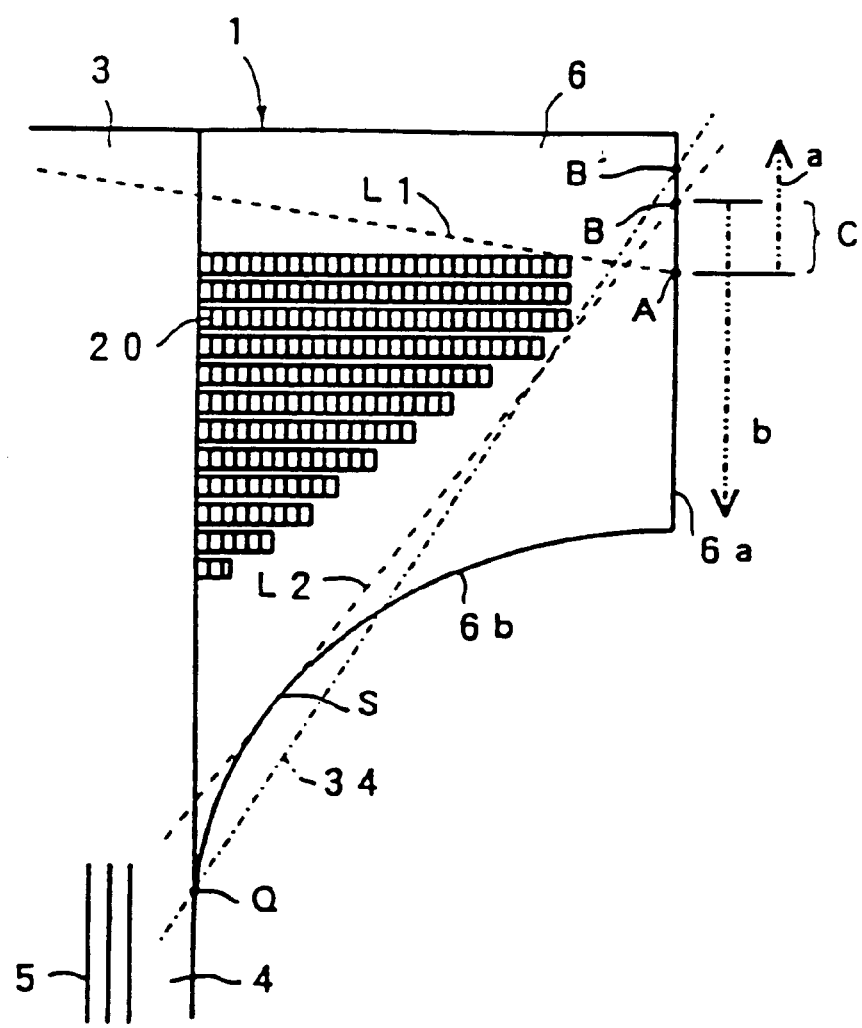
FIG. 26 is fragmentary development of a disposable diaper in accordance with the present invention showing a modification of the ear part, and a first side edge section a and a second side edge section b on the ear part.

A disposable diaper 1 in a fifth embodiment according to the present invention is provided with ear parts 6 each having a lower edge 6*b* having a lower curved portion S curved in the shape of a circular arc as shown in FIG. 26. A second boundary line L2 is tangent to the lower curved portion S of the lower edge 6*b* and a stress relaxing structure 20 and intersects the side edge 6*a* of the ear part 6 at an intersection point B. Therefore, a component tensile force of a tensile force applied to the ear part 6 at the intersection point B, acting along the second boundary line L2 can be transmitted to an absorbent part 3. A line 34 extended from the intersection point of the lower edge 6*b* of the ear part 6 and a side flap 4 extended along the side edge of an absorbent part 3 so as to be tangent to the stress relaxing structure 20 intersects the side edge 6*a* at an intersection point B'. The transmission of a component tensile force of a tensile force applied to the ear part 6 at the intersection point B' and transmitted along the line 34 is intercepted at the intersection point of the line 34 and the lower edge 6*b*. In this embodiment, a first side edge section a extends upward from the intersection point A, and a second side edge section b extends downward from the intersection point B. A pulling section R in which a fastener 7 is attached to the side edge 6*a* must overlap at least a section c between the intersection points A and B in which the first side edge section a and the second side edge section b overlap each other.

FIGS. 27 to 30 are fragmentary developments of disposable diapers in a sixth to ninth embodiment according to the present invention, which differ from the disposable diaper shown in FIG. 1 only in the direction of extension of the fastener. In each of the disposable diapers 1 of FIGS. 27 and 28, a fastener 7 is attached to the side edge 6*a* of an ear part 6 so as to extend at an inclination_meeting an inequality: 0<_<45°. In each of the disposable diapers 1 of FIGS. 29 and 30, a fastener 7 is attached to the side edge 6*a* of an ear part 6 so as to extend at an inclination_meeting an inequality: 0<_<45°.

Figure 27:
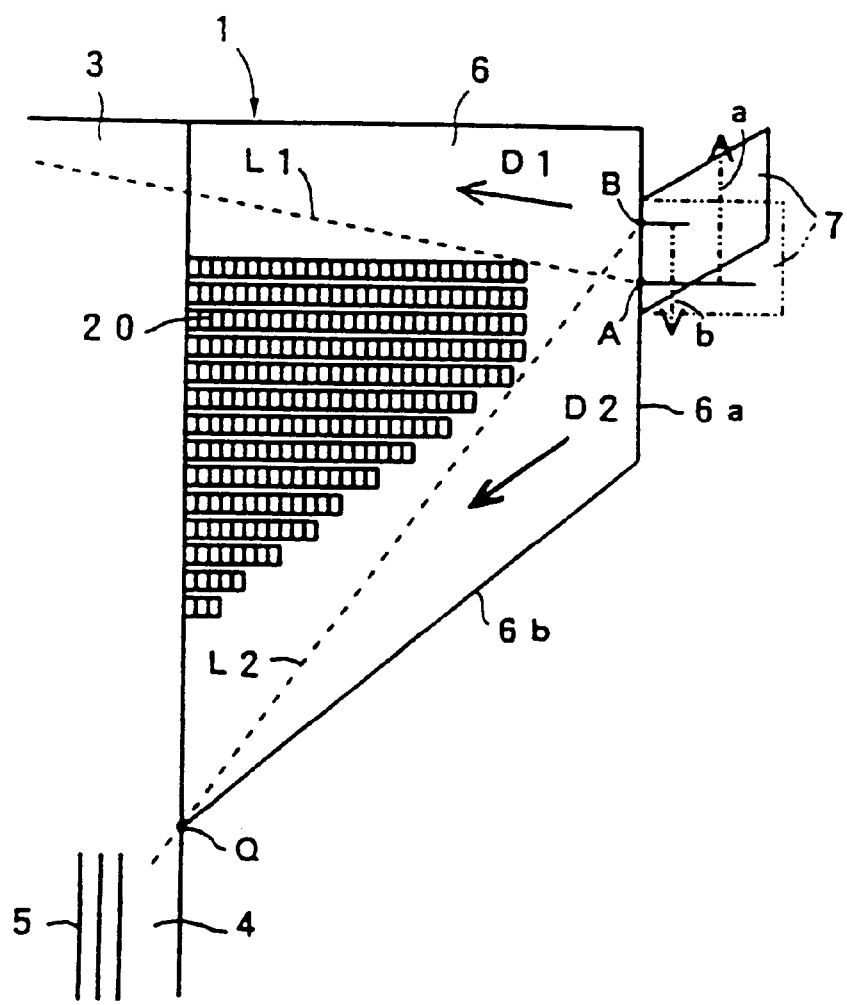
FIG. 27 is a fragmentary development of a disposable diaper in an embodiment according to the present invention provided with a fastening means extended obliquely upward from a position corresponding to that of the fastening means shown in FIG. 20.

When a tensile force D is applied to the fastener 7 attached to the side edge 6*a* of the ear part 6 as shown in FIG. 27 in the direction of extension of the fastener 7, a component tensile force D1 distributed to the waist lapping portion of an absorbent part 3 is smaller than a component tensile force D2 distributed to the leg lapping portion of the absorbent part 3. Since the fastener 7 is attached to the side edge 6*a* in a pulling section R overlapping both the first side edge section a and the second side edge section b, the tensile force D is distributed to both the waist lapping portion and the leg lapping portion.

Figure 28:
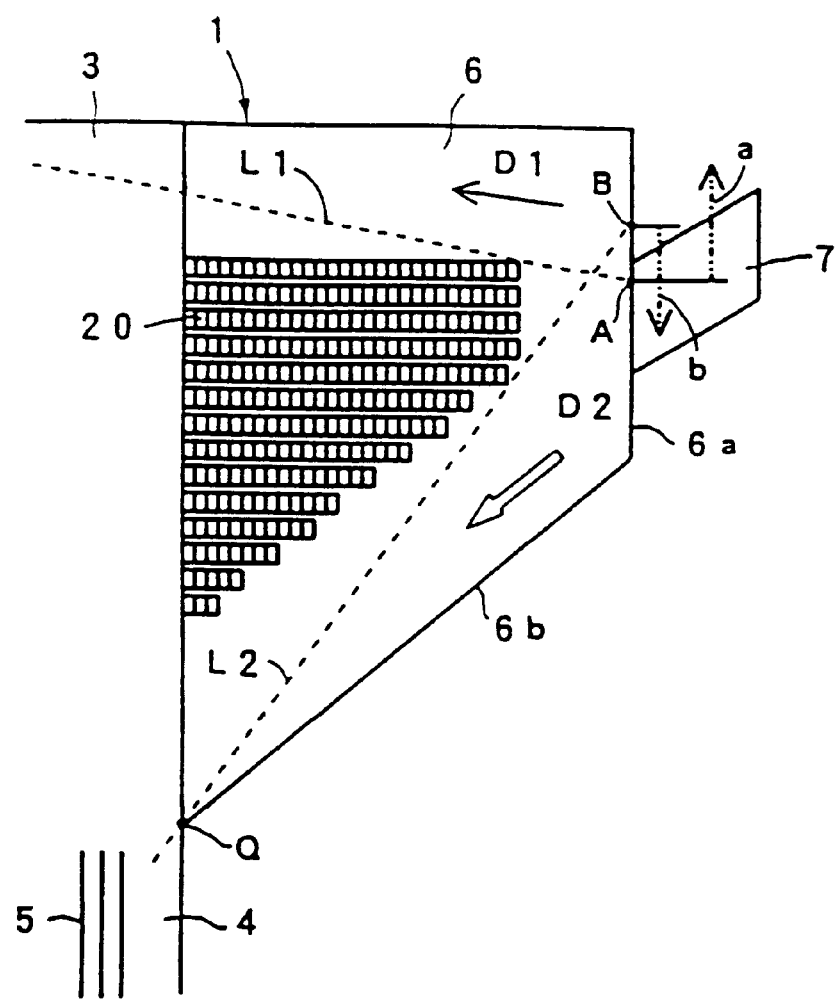
FIG. 28 is a fragmentary development of a disposable diaper in an embodiment according to the present invention provided with a fastening means extended obliquely upward from a position corresponding to that of the fastening means shown in FIG. 23.

In the disposable diaper 1 of FIG. 28, a portion of the pulling section R partly overlapping the second side edge section b is greater than that of the pulling section R partly overlapping the first side edge section a. Therefore, the component tensile force D2 distributed to the leg lapping portion is greater than the component tensile force D2 applied to the leg lapping portion of the disposable diaper shown in FIG. 27.

Figure 29:
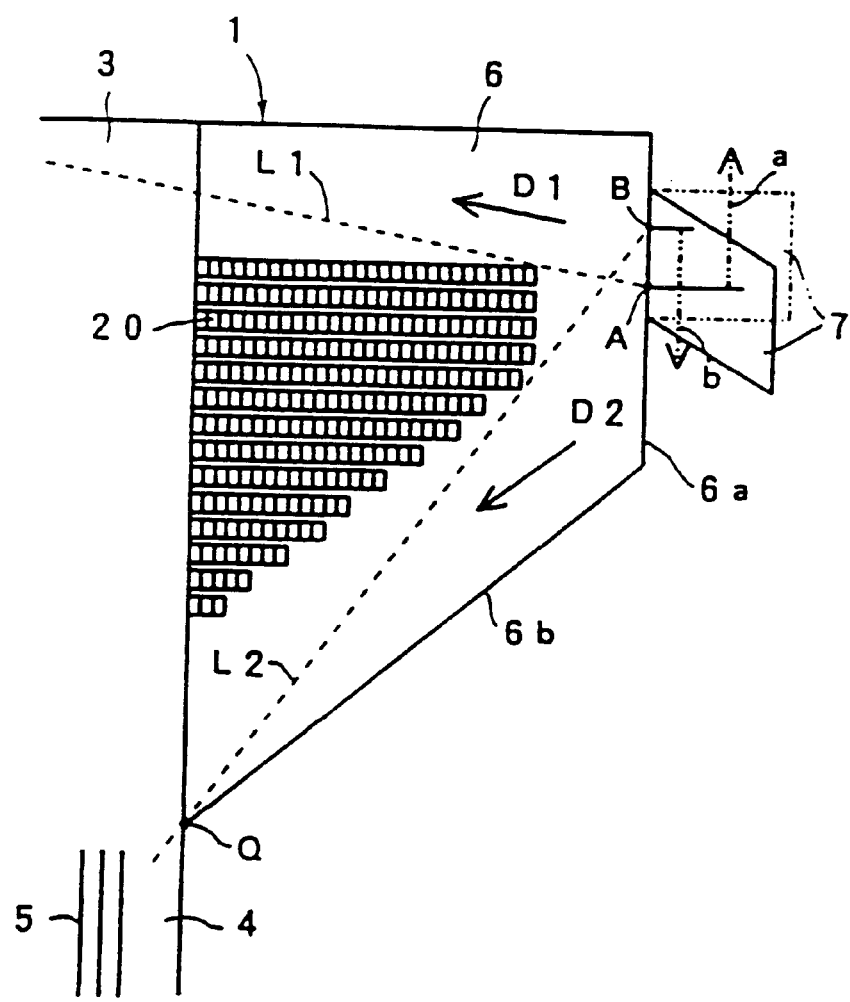
FIG. 29 is a fragmentary development of a disposable diaper in an embodiment according to the present invention provided with a fastening means extended obliquely downward from a position corresponding to that of the fastening means shown in FIG. 20.

When a tensile force D is applied to the fastener 7 attached to the side edge 6a of the ear part 6 as shown in FIG. 29 in the direction of extension of the fastener 7, a component tensile force D1 distributed to the waist lapping portion of an absorbent part 3 is greater than a component tensile force D2 distributed to the leg lapping portion of the absorbent part 3. Since the pulling section R overlaps both the first side edge section a and the second side edge section b, the component tensile force D2, though smaller than the component tensile force D1, can be distributed to the leg lapping portion.

Figure 30:
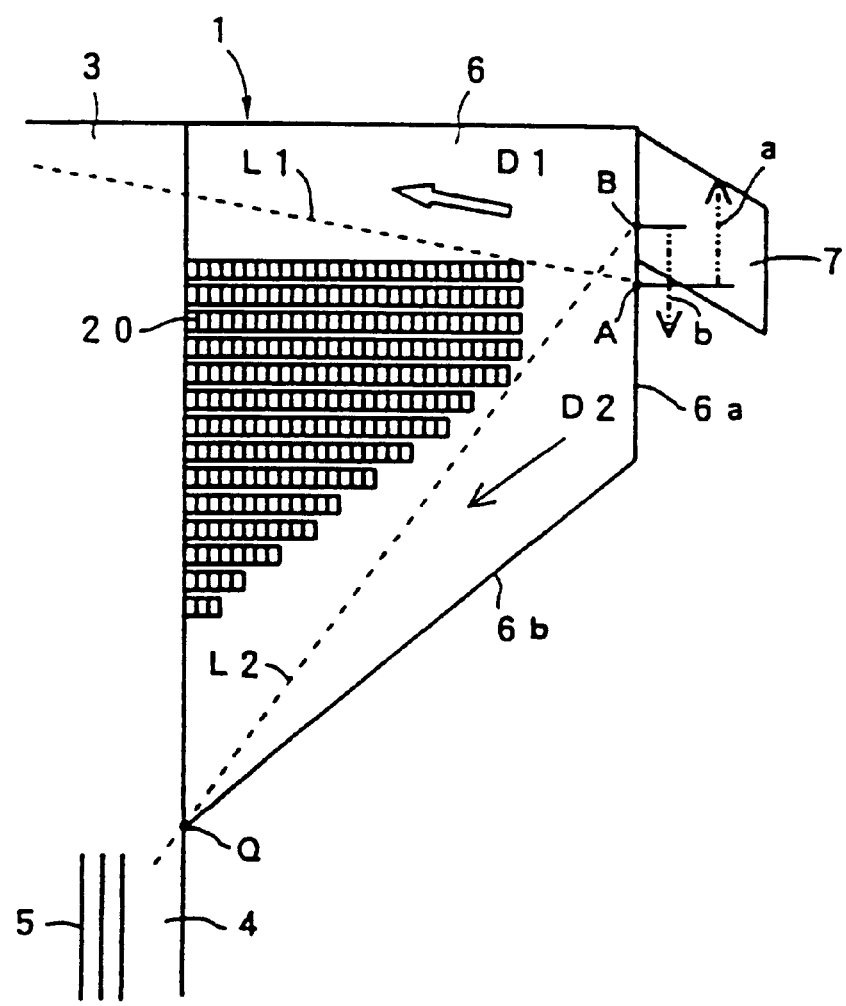
FIG. 30 is a fragmentary development of a disposable diaper in an embodiment according to the present invention provided with a fastening means extended obliquely downward from a position corresponding to that of the fastening means shown in FIG. 23.

In the disposable diaper 1 of FIG. 30, a portion of the pulling section R partly overlapping the first side edge section a is greater than that of the pulling section R partly overlapping the second side edge section b. There fore, the component tensile force D1 distributed to the waist lapping portion is greater than the component tensile force D2 applied to the waist lapping portion of the disposable diaper shown in FIG. 29.

Figure 31:
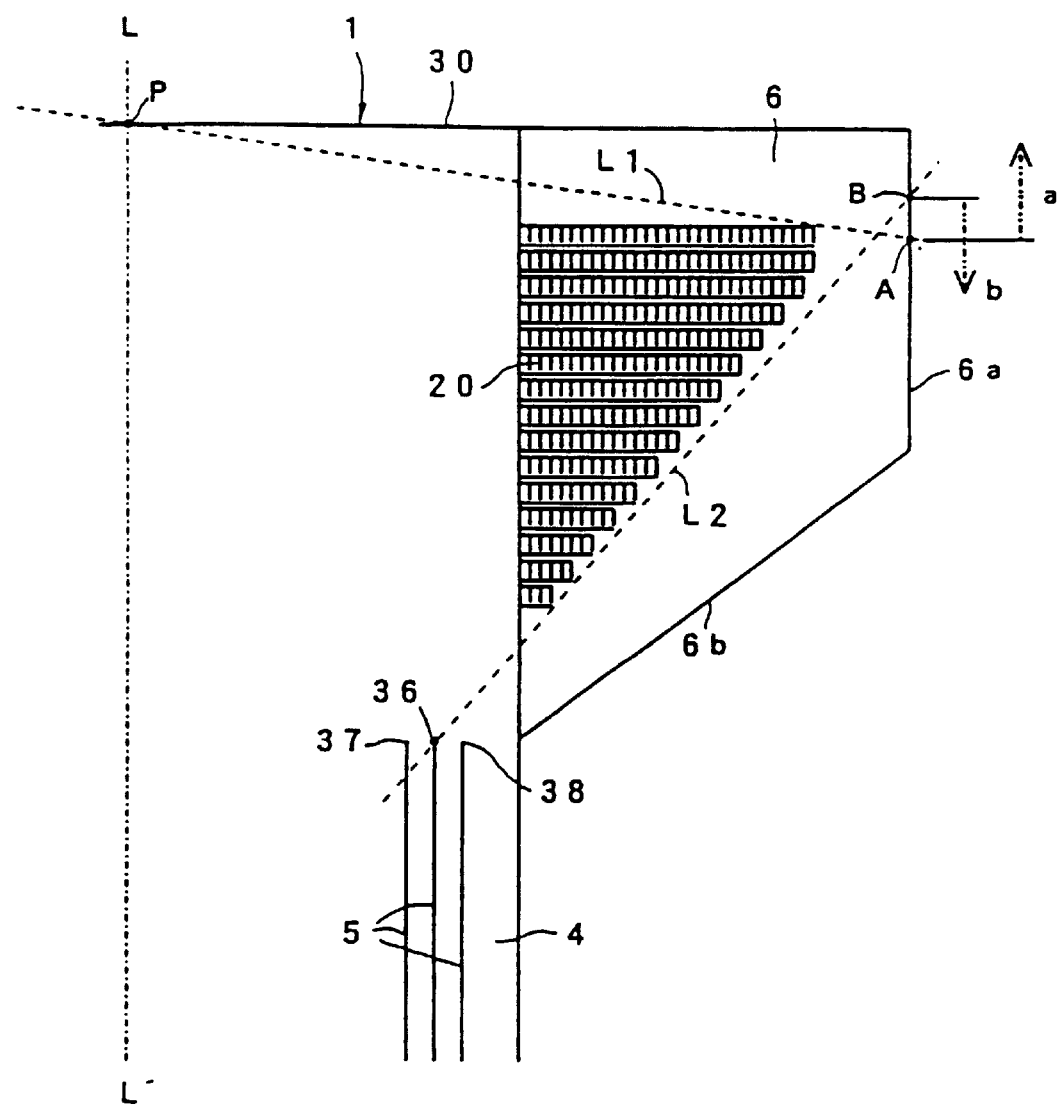
FIG. 31 is a fragmentary development of a disposable diaper, of assistance in explaining a method of defining a second edge section.
Figure 32:
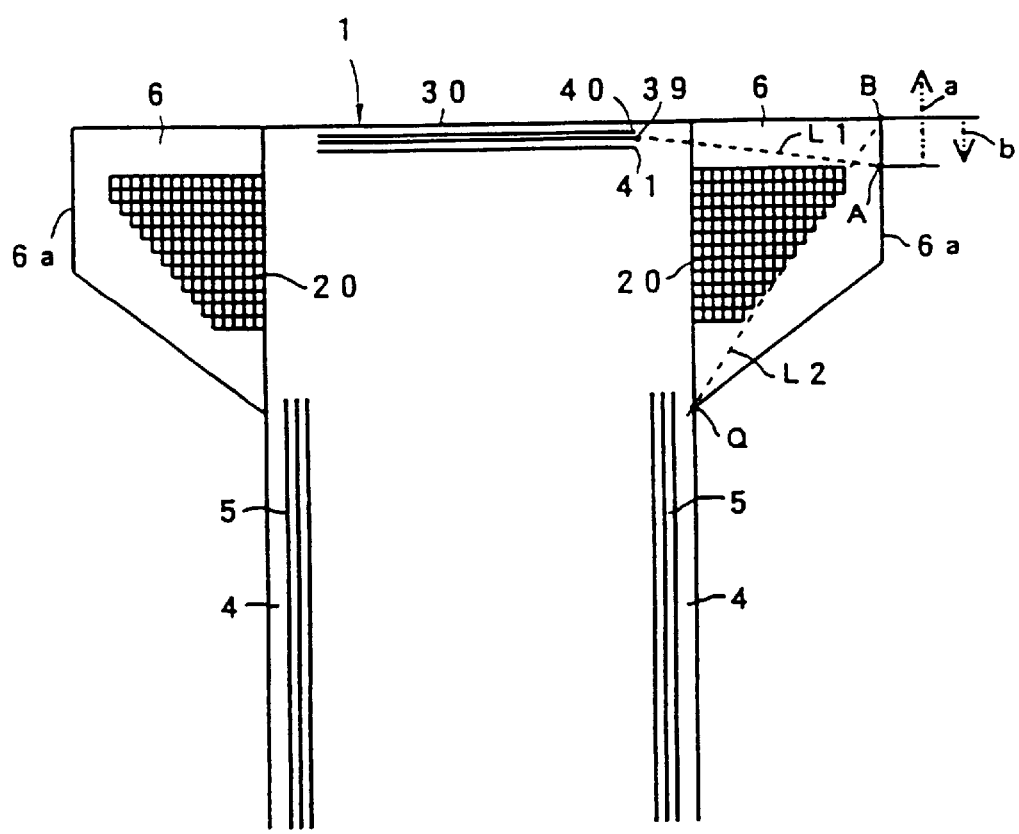
FIG. 32 is a fragmentary development of a disposable diaper, of assistance in explaining a method of defining a first side edge section.

FIGS. 31 and 32 show disposable diapers in a tenth and an eleventh embodiment according to the present invention. The disposable diaper 1 shown in FIG. 31 is similar in construction to that shown in FIG. 16, except that a second boundary line L2 in FIG. 31 for defining a second side edge section b is extended from the upper end 36 of the middle elastic leg fastening member 5 so as to be tangent to a stress relaxing structure 20 and intersects the side edge 6a of an ear part 6 at an intersection point B. Accordingly, part of a tensile force applied to the ear part 6 at the intersection point B acts directly on the upper end 36 of the middle elastic leg fastening member 5. The second boundary line L2 may be extended from the upper end 37 of the inner elastic leg fastening member 5 or the upper end 38 of the outer elastic leg fastening member 5. The disposable diaper 1 shown in FIG. 32 is similar in construction to that shown in FIG. 16, except that a first boundary line L1 in FIG. 32 for defining a first side edge section a is extended from the end 39 of the middle elastic waist fastening member 35 so as to be tangent to a stress relaxing structure 20 and intersects the side edge 6a of an ear part 6 at an intersection point A. Accordingly, part of a tensile force applied to the ear part 6 at the intersection point A acts directly on the ends 39 of the middle elastic waist fastening member 35. The first boundary line L1 may be extended from the end 40 of the upper elastic waist fastening member 35 or the end 41 of the lower elastic waist fastening member 35.

Figure 33:
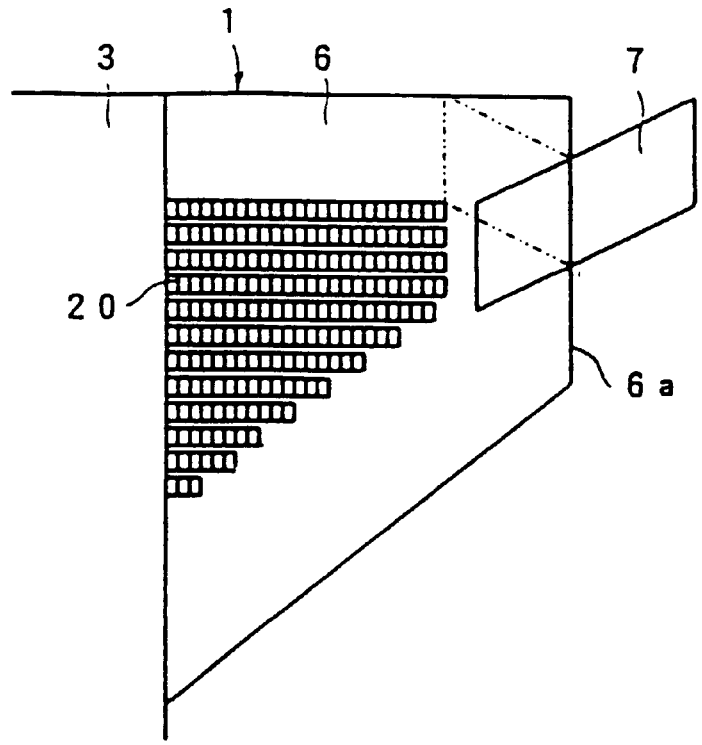
FIG. 33 is a fragmentary development of a disposable diaper in accordance with the present invention provided with a fastening means in a modification obliquely attached to an ear part.
Figure 34:
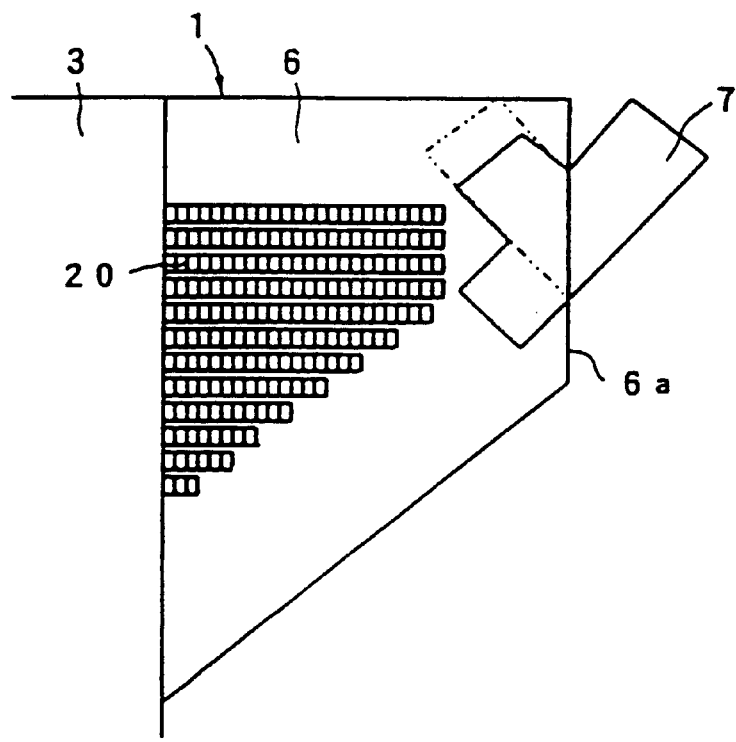
FIG. 34 is a fragmentary development of a disposable diaper in accordance with the present invention provided with a fastening means in a modification obliquely attached to an ear part.

The fastener 7 obliquely attached to the side edge 6a of the ear part 6 may be folded back at the middle thereof as indicated by broken lines as shown in FIG. 33 when packaging the disposable diaper and may project from the side edge 6a when the disposable diaper is unfolded for use. The fastener 7 may be formed in the shape of a fork and may be folded back as indicated by broken lines in FIG. 34. When thus folded back at the middle, no portion of the fastener 7 projects outward from the ear part 6. The fork-shaped fastener 7 shown in FIG. 34 ensures further reliable distribution of a tensile force applied thereto to the waist lapping portion and the leg lapping portion. Since the stress relaxing structure 20 is elastic, the stress relaxing structure 20 conforms easily to the shape of the hipbone and the like, which improves the wearing comfort of the wearer.

Although the invention has been described in its preferred forms with a certain degree of particularity, obviously many changes and variations are possible therein. It is therefore to be understood that the present invention may be practiced otherwise than as specifically described herein without departing from the scope and spirit thereof.

What is claimed is:
1. A disposable diaper comprising:
 (a) an absorbent part formed by sandwiching an absorbent core between a topsheet and a backsheet, and having a first longitudinal edge and a second longitudinal edge;
 (b) a pair of ear parts projecting laterally in opposite directions from said longitudinal edges, each said ear part having
  i) a side edge being generally parallel to said longitudinal edge,
  ii) an upper edge being generally perpendicular to said longitudinal edge,
  iii) a lower edge being nonparallel to said upper edge,
  iv) a stress relaxing structure extending laterally from said longitudinal edge, said stress relaxing structure being stretchable under a tensile force applied to said ear part and being capable of intercepting the transmission of said tensile force to said absorbent part,
  v) a first boundary line extending from said side edge to said upper edge, tangentially to said stress relaxing structure,
  vi) a waist lapping portion fastening component force distributing area being bounded by said first boundary line, said upper edge, and said side edge,
  vii) a first side edge section extending along said side edge and forming said waist fastening component force distributing area,
  viii) a second boundary line extending from said side edge to a point of intersection of said lower edge and said longitudinal edge, tangentially to said stress relaxing structure,
  ix) a leg lapping portion fastening component force distributing area being bounded by said second boundary line, said lower edge, and said side edge,
  x) a second edge section extending along said side edge and forming said leg fastening component force distributing area; and
  xi) a peripheral portion including said waist and said leg lapping portion fastening component force distributing areas, said waist and said leg lapping portion fastening component force distributing areas surrounding said stress relaxing structure, said peripheral portion being virtually unstretchable under said tensile force, and
 (c) a pair of fasteners, each said fastener being attached to said side edge of one of said ear part and overlapping at least part of said first side edge section and said second side edge section.
2. A disposable diaper according to claim 1, wherein said stress relaxing structure has a substantially trapezoidal shape.
3. A disposable diaper according to claim 2, wherein said lower edge of said stress relaxing structure is arcuate.
4. A disposable diaper according to claim 1, wherein said stress relaxing structure forms a part of an ellipse or a part of a circle.

5. A disposable diaper according to claim 4, wherein said lower edge of said stress relaxing structure is arcuate.

6. A disposable diaper according to any of claims 2, 3, 4, or 5, wherein said stress relaxing structure has a plurality of undeformed sections, a plurality of permanently deformed sections, and transitional sections between said undeformed sections and said permanently deformed sections.

7. A disposable diaper according to claim 1, wherein said stress relaxing structure has a plurality of logitudinal slits.

8. A disposable diaper according to claim 7, wherein said lower edge of said stress relaxing structure is arcuate.

9. A disposable diaper according to claim 1, wherein said stress relaxing structure has at least one logitudinal slit.

10. A disposable diaper according to claim 9, wherein said lower edge of said stress relaxing structure is arcuate.

* * * * *